US008524453B2

(12) United States Patent
Stahl et al.

(10) Patent No.: US 8,524,453 B2
(45) Date of Patent: Sep. 3, 2013

(54) LECTIN COMPLEMENT PATHWAY ASSAYS AND RELATED COMPOSITIONS AND METHODS

(75) Inventors: Gregory L. Stahl, Clinton, MA (US); Mary C. Walsh, Brighton, MA (US)

(73) Assignee: The Brigham and Woman's Hospital, Inc., Boston, MA (US)

( * ) Notice: Subject to any disclaimer, the term of this patent is extended or adjusted under 35 U.S.C. 154(b) by 580 days.

(21) Appl. No.: 12/223,763

(22) PCT Filed: Feb. 9, 2007

(86) PCT No.: PCT/US2007/003644
§ 371 (c)(1),
(2), (4) Date: Feb. 3, 2009

(87) PCT Pub. No.: WO2007/095154
PCT Pub. Date: Aug. 23, 2007

(65) Prior Publication Data
US 2009/0305306 A1    Dec. 10, 2009

Related U.S. Application Data

(60) Provisional application No. 60/771,880, filed on Feb. 10, 2006.

(51) Int. Cl.
*G01N 33/53* (2006.01)
(52) U.S. Cl.
USPC .............................................. 435/7.1; 436/518
(58) Field of Classification Search
None
See application file for complete search history.

(56) References Cited

U.S. PATENT DOCUMENTS

| | | | |
|---|---|---|---|
| 2,414,747 | A | 1/1947 | Kirachbanm |
| 3,734,091 | A | 5/1973 | Taplin |
| 4,326,513 | A | 4/1982 | Schulz et al. |
| 4,642,284 | A | 2/1987 | Cooper et al. |
| 4,648,397 | A | 3/1987 | Beale |
| 4,665,911 | A | 5/1987 | Williams et al. |
| 4,870,061 | A | 9/1989 | Speck |
| 4,889,116 | A | 12/1989 | Taube |
| 4,960,712 | A | 10/1990 | Theofilopoulos et al. |
| 5,103,814 | A | 4/1992 | Maher |
| 5,270,199 | A | 12/1993 | Ezekowitz |
| 5,365,922 | A | 11/1994 | Raemer |
| 5,437,977 | A | 8/1995 | Segev |
| 5,616,311 | A | 4/1997 | Yen et al. |
| 5,766,632 | A | 6/1998 | Oldham et al. |
| 6,084,060 | A | 7/2000 | Moore |
| 6,087,120 | A | 7/2000 | Van Oeveren et al. |
| 6,235,494 | B1 | 5/2001 | Hugli |
| 6,280,724 | B1 | 8/2001 | Moore |
| 6,297,024 | B1 | 10/2001 | Hugli et al. |
| 6,310,195 | B1 | 10/2001 | Colucci et al. |
| 6,572,856 | B1 | 6/2003 | Taylor et al. |
| 6,969,601 | B2 * | 11/2005 | Jensenius et al. ............. 435/226 |
| 7,211,396 | B2 | 5/2007 | Uttenthal |
| 7,273,925 | B1 | 9/2007 | Stahl et al. |
| 2002/0082208 | A1 | 6/2002 | Jensenius et al. |
| 2002/0082209 | A1 | 6/2002 | Jensenius et al. |
| 2003/0143223 | A1 | 7/2003 | Cabezas et al. |
| 2004/0038297 | A1 | 2/2004 | Jensenius et al. |
| 2004/0259771 | A1 | 12/2004 | Stahl et al. |
| 2005/0019326 | A1 | 1/2005 | Stahl |
| 2005/0032157 | A1 | 2/2005 | Gal et al. |
| 2005/0037441 | A1 | 2/2005 | Ahearn et al. |
| 2005/0042602 | A1 | 2/2005 | Ahearn et al. |
| 2006/0002937 | A1 | 1/2006 | Schwaeble et al. |
| 2007/0009528 | A1 | 1/2007 | Larsen et al. |
| 2007/0065415 | A1 | 3/2007 | Kleinsek et al. |
| 2007/0172483 | A1 | 7/2007 | Schwaeble et al. |
| 2007/0178068 | A1 | 8/2007 | Reich et al. |
| 2011/0293524 | A1 | 12/2011 | Stahl |

FOREIGN PATENT DOCUMENTS

| | | |
|---|---|---|
| EP | 0 303 502 A1 | 2/1989 |
| EP | 0 492 530 A1 | 7/1992 |
| GB | 2408573 A | 6/2005 |
| JP | 6-121695 A | 5/1994 |
| JP | 7-238100 A | 9/1995 |
| WO | WO 85/01442 A1 | 4/1985 |
| WO | WO 89/01519 A1 | 2/1989 |
| WO | WO 90/08549 A1 | 8/1990 |
| WO | WO 91/06010 A1 | 5/1991 |
| WO | WO 93/18775 A1 | 9/1993 |
| WO | WO 95/31728 A1 | 11/1995 |
| WO | WO 97/28276 A1 | 8/1997 |
| WO | WO 97/31121 A1 | 8/1997 |
| WO | WO 99/39209 A1 | 8/1999 |
| WO | WO 99/64453 A1 | 12/1999 |
| WO | WO 99/66321 A2 | 12/1999 |
| WO | 00/22160 A1 | 4/2000 |
| WO | 00/35483 A1 | 6/2000 |
| WO | 00/72023 A2 | 11/2000 |

(Continued)

OTHER PUBLICATIONS

Takahashi et al. International Immunology 1999 vol. 11, p. 859-863.*
[No Author Listed] Alexion Pharmaceuticals & Brigham and Women's Hospital scientists demonstrate new pathway for complement activation in cardiovascular disease. Press release dated May 3, 2000. http://www.alexionpharm.com/news/sub_press.cfm?prid=172 &selectyear=2000. Last accessed Nov. 8, 2000. 3 pages.
[No Author Listed] Alexion Pharmaceuticals: Complement inhibitors. http://www.alexionpharm.com/techplat/complement.cfm.Last accessed Nov. 8, 2000. 2 pages.
[No Author Listed] Alexion Pharmaceuticals: Product profiles: Myocardial infarction. http://www.alexionpharm.com/products/mi.cfm.Last accessed Nov. 8, 2000. 1 page.
[No Author Listed] Inside Industry. New Inflammatory Pathway Discovered. Alexion Pharma and Brigham & Women's Hospital Report on Cardiovascular Studies. Genetic Engineering News. May 15, 2000;20(3): 27, 64, 88.

(Continued)

*Primary Examiner* — Jacob Cheu
(74) *Attorney, Agent, or Firm* — Wolf, Greenfield & Sacks, P.C.

(57) ABSTRACT

This invention is related, in part, to assays for analyzing the lectin complement pathway (LCP) as well as to compositions and methods related thereto.

24 Claims, 17 Drawing Sheets

(56) References Cited

FOREIGN PATENT DOCUMENTS

| WO | 01/12212 A1 | 2/2001 |
|---|---|---|
| WO | 02/22161 A2 | 3/2002 |
| WO | 03/022223 A2 | 3/2003 |
| WO | 03/068150 A2 | 8/2003 |
| WO | 2004/011674 A1 | 2/2004 |
| WO | 2004/075837 A2 | 9/2004 |
| WO | 2004/112572 A2 | 12/2004 |
| WO | 2005/005630 A2 | 1/2005 |
| WO | 2006/120160 A1 | 11/2006 |

OTHER PUBLICATIONS

[No Author Listed] Read a story about complement in The Economist. Letter to shareholders and interested parties from Leonard Bell, MD, President and CEO of Alexion Pharmaceuticals, Inc. http://www.alexionpharm.com/news/sub_press.cfm?prid=174&selectyear=2000. Last accessed Nov. 8, 2000. 2 pages.
[No Author Listed] Scientific study published in Journal of Clinical Investigation demonstrates terminal complement activation causes kidney damage during ischemia and reperfusion. Press release dated May 15, 2000. http://www.alexionpharm.com/news/sub_press.cfm?prid=173&selectyear=2000. Last accessed Nov. 8, 2000. 3 pages.
[No Author Listed]. Alexion Pharmaceuticals and the Brigham and Women's Hospital form collaboration to develop novel anti-inflammatory antibody. Press release dated Feb. 15, 2000. http://www.alexionpharm.com/news/sub_press.cfm?prid=159&selectyear=2000. Last accessed Nov. 8, 2000. 3 pages.
Agah et al., Isolation, Characterization, and Cloning of Porcine Complement Component C7. J Immunol. 2000:1059-65.
Agah et al., Isolation, cloning and functional characterization of porcine mannose-binding lectin. Immunology. Mar. 2001;102(3):338-43.
Albert et al., Plasma levels of cystatin-C and mannose binding protein are not associated with risk of developing systemic atherosclerosis. Vasc Med. 2001;6(3):145-9.
Alencar et al., Leguminous lectins as tools for studying the role of sugar residues in leukocyte recruitment. Mediators Inflamm. 1999;8(2):107-13.
Amsterdam et al., Limitation of reperfusion injury by a monoclonal antibody to C5a during myocardial infarction in pigs. Am J Physiol. Jan. 1995;268(1 Pt 2):H448-57.
Atkinson et al., L-ficolin in children with recurrent respiratory infections. Clin Exp Immunol. Dec. 2004;138(3):517-20.
Azofra et al., C4 deficiency in chronic angioedema. Allergy. Nov. 2001;56(11):1106-7.
Baccarelli et al., Mannose-binding lectin-2 genetic variation and stomach cancer risk. Int J Cancer. Oct. 2006, 15;119(8):1970-5.
Bathum et al., Association between combined properdin and mannose-binding lectin deficiency and infection with Neisseria meningitidis. Mol Immunol. Feb. 2006;43(5):473-9. Epub Mar. 21, 2005.
Bax et al., Association of familial deficiency of mannose-binding lectin and meningococcal disease. Lancet. Sep. 25, 1999;354(9184):1094-5.
Berger et al., Low pretransplantation mannose-binding lectin levels predict superior patient and graft survival after simultaneous pancreas-kidney transplantation. J Am Soc Nephrol. Aug. 2007;18(8):2416-22. Epub Jul. 18, 2007.
Best et al., Prospective analysis of mannose-binding lectin genotypes and coronary artery disease in American Indians: the Strong Heart Study. Circulation. Feb. 3, 2004;109(4):471-5. Epub Jan. 19, 2004.
Bhole et al., Therapeutic potential of targeting the complement cascade in critical care medicine. Crit Care Med. Jan. 2003;31(1 Suppl):S97-104. Review. Abstract Only.
Blume et al., Activated endothelial cells elicit paracrine induction of epithelial chloride secretion. 6-Keto-PGF1alpha is an epithelial secretagogue. J Clin Invest. Sep. 15, 1998;102(6):1161-72.
Borzy et al., Inherited C3 deficiency with recurrent infections and glomerulonephritis. Am J Dis Child. Jan. 1998;142(1):79-83.
Bouwman et al., Elevated levels of mannose-binding lectin at clinical manifestation of type 1 diabetes in juveniles. Diabetes. Oct. 2005;54(10):3002-6.
Brouwer et al., Mannan-binding lectin (MBL)-mediated opsonization is enhanced by the alternative pathway amplification loop. Mol Immunol. May 2006;43(13):2051-60. Epub Feb. 24, 2006.
Brown et al., Influence of donor C3 allotype on late renal-transplantation outcome. n. Engl J Med. May 11, 2006;354(19):2014-23.
Busche et al., Mannonse-binding lectin plays a critical role in diabetic cardiomyopathy, hypertrophic remodeling and myocardial ischemia and reperfusion injury. Molecular Immunology. 2007;44(16)):3912. Abstract Only.
Calvo-Alen et al., Systemic lupus erythematosus in a multiethnic US cohort: XXXIV. Deficient mannose-binding lectin exon 1 polymorphisms are associated with cerebrovascular but not with other arterial thrombotic events. Arthritis Rheum. Jun. 2006;54(6):1940-5.
Casset et al., A peptide mimetic of an anti-CD4 monoclonal antibody by rational design. Biochem Biophys Res Commun. Jul. 18, 2003;307(1):198-205.
Cedzynski et al., Mannan-binding lectin insufficiency in children with recurrent infections of the respiratory system. Clin Exp Immunol. May 2004;136(2):304-11.
Chaka et al., Induction of TNF-alpha in human peripheral blood mononuclear cells by the mannoprotein of Cryptococcus neoformans involves human mannose binding protein. J Immunol. Sep. 15, 1997;159(6):2979-85.
Chandra et al., Structural Similarity and Functional Diversity in Proteins Containing the Legume Lectin Fold. Protein Engineering. 2001;14(11):857-66.
Chatterjee et al., Idiotypic antibody immunotherapy of cancer. Cancer Immunol Immunother. Feb. 1994;38(2):75-82. Review.
Christiansen et al., Mannan-binding lectin deficiency is associated with unexplained recurrent miscarriage. Scand J Immunol. Feb. 1999;49(2):193-6.
Cochlovius et al., Therapeutic Antibodies. After years of promise, magic bullets appear to be on the upswing. Modern Drug Discovery. 2003:33-34, 37-38.
Collard et al., Complement activation after oxidative stress: role of the lectin complement pathway. Am J Pathol. May 2000;156(5):1549-56.
Collard et al., Complement activation following oxidative stress. Mol Immunol. Sep.-Oct. 1999;36(13-14):941-8. Review.
Collard et al., Complement activation following reoxygenation of hypoxic human endothelial cells: role of intracellular reactive oxygen species, NF-kappaB and new protein synthesis. Immunopharmacology. Mar. 1998;39(1):39-50.
Collard et al., Endothelial oxidative stress activates the lectin complement pathway: role of cytokeratin 1. Am J Pathol. Sep. 2001;159(3):1045-54.
Collard et al., Endothelial oxidative stress increases cytokeratin 1 (K1) expression and human mannose-binding (MBL) deposition. Print Meeting Info: XVIIITH International Complement Workshop, Salt Lake City, Utah, USA, Jul. 23-27, 2000. Immunopharmacology. 2000;49(1-2):85. Abstract Only.
Collard et al., Endothelial reoxygenation activates the lectin complement pathway. Inhibition with anti-human mannose binding lectin (MBL) therapy. Meeting Info: 7th European Meeting on Complement in Human Disease, Helsinki, Finland, Jun. 17-20, 1999; *Molecular Immunology*. 1999;36(4-5):278. Abstract Only.
Collard et al., Hypoxia-induced expression of complement receptor type 1 (CR1, CD35) in human vascular endothelial cells. AJP-Cell Physiology. 1999;276(2):C450-58.
Collard et al., Reoxygenation of hypoxic human umbilical vein endothelial cells activates the classic complement pathway. Circulation. Jul. 1, 1997;96(1):326-33.
Collard et al., Reoxygenation of hypoxic human umbillical vein endothelial cells (HUVECs) activates the lectin complement pathway (LCP). Meeting Info: Annual Meeting of Professional Research Scientists on Experimental Biology 98, Part 1, San Francisco, CA, USA, Apr. 18-22, 1998, Federation of American Societies of Ex. FASEB Journal. 1998;12(4):A29. Abstract Only.

Colucci et al., cDNA cloning of FRIL, a lectin from Dolichos lablab, that preserves hematopoietic progenitors in suspension culture. Proc Natl Acad Sci U S A. Jan. 19, 1999;96(2):646-50.

Czermak et al., Protective effects of C5a blockade in sepsis. Nat Med. Jul. 1999;5(7):788-92.

Da Silva et al., Homozygous hereditary C3 deficiency due to a premature stop codon. J Clin Immunol. Nov. 2002;22(6):321-30.

Dahl et al., MASP-3 and its association with distinct complexes of the mannan-binding lectin complement activation pathway. Immunity. Jul. 15, 2001; (1):127-35.

De Silva et al., APT070 inhibits complement activation during in vitro cardiopulmonary bypass. Eur J Cardiothorac Surg. Jul. 30, 2006; (1):72-6. Epub May 24, 2006.

De Vries et al., The mannose-binding lectin-pathway is involved in complement activation in the course of renal ischemia-reperfusion injury. Am J Pathol. Nov. 2003;165(5):1677-88.

Dean et al., Heteroligomeric forms of codon 54 mannose binding lectin (MBL) in circulation demonstrate reduced in vitro function. Mol Immunol. Mar. 2006;43(7):950-61. Epub Aug. 11, 2005.

Endo et al., Exon structure of the gene encoding the human mannose-binding protein-associated serine protease light chain: comparison with complement C1r and C1s genes. Int Immunol. Sep. 8, 1996; (9):1355-8.

Endo et al., Glomerular deposition of mannose-binding lectin (MBL) indicates a novel mechanism of complement activation in IgA nephropathy. Nephrol Dial Transplant. 1998;13(8):1984-90.

Endo et al., Regulation of in situ complement activation via the lectin pathway in patients with IgA nephropathy. Clin Nephrol. Mar. 2001;55(3):185-91.

Endo et al., Two lineages of mannose-binding lectin-associated serine protease (MASP) in vertebrates. J Immunol. Nov. 1, 1998;161(9):4924-30.

Fiane et al., Mechanism of complement activation and its role in the inflammatory response after thoracoabdominal aortic aneurysm repair. Circulation. Aug. 19, 2003;108(7):849-56. Epub Aug. 4, 2003.

Fischer et al., Mannan-binding protein and bovine conglutinin mediate enhancement of herpes simplex virus type 2 infection in mice. Scand J Immunol. May 1994;39(5):439-45.

Fishelson et al., Complement and apoptosis. Mol Immunol. Aug. 2001;38(2-3):207-19.

Fitch et al., Pharmacology and Biological Efficacy of a Recombinant, Humanized, Single-Chain Antibody C5 Complement Inhibitor in Patients Undergoing Coronary Artery Bypass Graft Surgery with Cardiopulmonary Bypass. Circulation. Dec. 21-28, 1999:2499-2506.

Font et al., Association of mannose-binding lectin gene polymorphisms with antiphospholipid syndrome, cardiovascular disease and chronic damage in patients with systemic lupus erythematosus. Rheumatology (Oxford). Jan. 2007;46(1):76-80. Epub Jun. 26, 2006.

Foster et al., Ulex europaeus 1 lectin targets microspheres to mouse Peyer's patch M-cells in vivo. Vaccine. Mar. 1998;16(5):536-41.

Frederiksen et al., Quantification of mannan-binding lectin. J Immunol Methods. Aug. 31, 2006;315(1-2):49-60. Epub Jul. 31, 2006.

Gabor et al., Lectin-mediated bioadhesion: binding characteristics of plant lectins on the enterocyte-like cell lines Caco-2, HT-29 and HCT-8. J Control Release. Nov. 13, 1998;55(2-3):131-42.

Gadjeva et al., Mannan-binding lectin—a soluble pattern recognition molecule. Mol Immunol. Jun. 2004;41(2-3):113-21.

Garred et al., Mannose-binding lectin polymorphisms and susceptibility to infection in systemic lupus erythematosus. Arthritis Rheum. Oct. 1999;42(10):2145-52.

Garred et al., Two edged role of mannose binding lectin in rheumatoid arthritis: a cross sectional study. J Rheumatol. Jan. 27, 2000; (1):26-34.

Gherghiceanu et al., The predictive value of peritubular capillaries C3d deposition in IgA glomerulonephritis. J Cell Mol Med. Jan.-Mar. 2005;9(1):143-52.

Gibbs et al., P-selectin mediates intestinal ischemic injury by enhancing complement deposition. Surgery. Jun. 1996;119(6):652-6.

Gomi et al., Mannose-binding lectin gene polymorphism is a modulating factor in repeated respiratory infections. Chest. Jul. 2004;126(1):95-9.

Graudal et al., Mannan binding lectin in rheumatoid arthritis. A longitudinal study. J Rheumatol. Apr. 1998;25(4):629-35.

Gupta et al., Association of mannose-binding lectin gene (MBL2) polymorphisms with rheumatoid arthritis in an Indian cohort of case-control samples. J Hum Genet. 2005;50(11):58391. Epub Oct. 12, 2005.

Hansen et al., Association between mannose-binding lectin and vascular complications in type 1 diabetes. Diabetes. Jun. 2004;53(6):1570-6.

Hansen et al., Elevated levels of mannan-binding lectin in patients with type 1 diabetes. J Clin Endocrinol Metab. Oct. 2003;88(10):4857-61.

Hansen et al., Mannose-binding lectin and mortality in type 2 diabetes. Arch Intern Med. Oct. 9, 2006;166(18):2007-13.

Hansen, Mannose-binding lectin (MBL) and vascular complications in diabetes. Horm Metab Res. Apr. 2005;37 Suppl 1:95-8.

Harboe et al., The quantitative role of alternative pathway amplification in classical pathway induced terminal complement activation. Clin Exp Immunol. Dec. 2004;138(3):439-46.

Hart et al., Gastrointestinal ischemia-reperfusion injury is complement-dependent but not dependent on C1q. Mol Immunl. 2003;40:187. Abstract Only.

Hart et al., Gastrointestinal ischemia-reperfusion injury is lectin complement pathway dependent without involving C1q. J Immunol. May 15, 2005;174(10):6373-80.

Hart et al., Initiation of complement activation following oxidative stress. In vitro and in vivo observations. Mol Immunol. Jun. 2004;41(2-3):165-71. Review.

Hasan et al., Identification of cytokeratin 1 as a binding protein and presentation receptor for kininogens on endothelial cells. Proc Natl Acad Sci U S A. Mar. 31, 1998;95(7):3615-20.

Hegele et al., Infection-susceptibility alleles of mannose-binding lectin are associated with increased carotid plaque area. J Investig Med. May 2008;48(3):198-202.

Hisano et al., Activation of the lectin complement pathway in Henoch-Schönlein purpura nephritis. Am J Kidney Dis. Feb. 2005;45(2):295-302.

Hisano et al., Mesangial IgA2 deposits and lectin pathway-mediated complement activation in IgA glomerulonephritis. Am J Kidney Dis. Nov. 2001;38(5):1082-8.

Hober et al., Coxsackievirus B3-induced chronic myocarditis in mouse: use of whole blood culture to study the activation of TNF alpha-producing cells. Microbiol Immunol. 1996;40(11):837-45.

Hovind et al., Mannose-binding lectin as a predictor of microalbuminuria in type 1 diabetes: an inception cohort study. Diabetes. May 2005;54(5):1523-7.

Jack et al., Activation of complement by mannose-binding lectin on isogenic mutants of Neisseria meningitidis serogroup B. J Immunol. Feb. 1, 1998;160(3):1346-53.

Janeway et al., 13-11 (last 3 paragraphs) to 13-13 (first 4 lines of second paragraph). In: Immunobiology. 3d ed. Garland Press. 1997. 3 pages.

Janeway et al., 13-6 (end of section) to 13-7 (first four paragraphs). In: Immunobiology. 3d ed. Garland Press. 1997. 2 pages.

Janeway et al., 3-19 (last paragraph) to 3-20. In: Immunobiology. 3d ed. Garland Press. 1997. 2 pages.

Janeway et al., 3-6 (last paragraph) to 3-7 (first two paragraphs). In: Immunobiology. 4th ed. 1999:87.

Janeway et al., The distribution and functions of immunoglobulin isotypes. In: Immunobiology. 3d ed. Garland Press. 1997. 2 pages.

Jablonska-Skwiecinska et al., Clinical trial of mannose treatment of hemolytic anemia caused by congenital deficiency of erythrocyte glucosephosphate isomerase Acta Haematol Pol. 1992;23(2):123-8. Polish.

Jones et al., Vascular smooth muscle polyploidization as a biomarker for aging and its impact on differential gene expression. J Biol Chem. Feb. 13, 2004;279(7):5306-13. Epub Nov. 22, 2003.

Jordan et al, Inhibition of mannose-binding lectin reduces postischemic myocardial reperfusion injury. Circulation. Sep. 18, 2001;104(12):1413-8.

Karpel-Massler et al., Human C1 esterase inhibitor attenuates murine mesenteric ischemia/reperfusion induced local organ injury. J Surg Res. Dec. 2003;115(2):247-56.

Kaur et al., Elevated levels of mannan-binding lectin [corrected] (MBL) and eosinophilia in patients of bronchial asthma with allergic rhinitis and allergic bronchopulmonary aspergillosis associate with a novel intronic polymorphism in MBL. Clin Exp Immunol. Mar. 2006;143(3):414-9. Erratum in Clin Exp Immunol. Jun. 2006;144(3):552.

Kingman, Complement activation in myocardial infarction: A target for future treatments? Drug Discovery Today. 2000; 8: 313-4.

Konami et al., Correlation between carbohydrate-binding specificity and amino acid sequence of carbohydrate-binding regions of Cytisus-type anti-H(O) lectins. FEBS Lett. Jun. 15, 1992;304(23):129-35.

Kuipers et al., A case of familial meningococcal disease due to deficiency in mannose-binding lectin (MBL). Adv Exp Med Biol. 2003;531:351-5.

Kuntz, Structure-based strategies for drug design and discovery. Science. Aug. 21, 1992;257(5073):1078-82.

Lanzrein et al., Mannan-binding lectin in human serum, cerebrospinal fluid and brain tissue and its role in Alzheimer's disease. Neuroreport. May 11, 1998;9(7):1491-5.

Lekowski et al., Ulex europaeus agglutinin II (UEA-II) is a novel, potent inhibitor of complement activation. Protein Sci. Feb. 2001;10(2):277-84.

Lekowski et al., Ulex europaeus Agglutinin II (UEA-II) is a novel, potent inhibitor of complement activation on human endothelial cells. 72nd Scientific Sessions of the American Heart Association. Atlanta, Georgia, USA. Nov. 7-10, 1999. Circulation. Nov. 2, 1999;100(18 Suppl):1.259. Abstract Only.

Lennon et al., Complement-induced endothelial dysfunction in rabbits: mechanisms, recovery, and gender differences. Am J Physiol. Jun. 1996;270(6 Pt 2):H1924-32.

Lhotta et al., Glomerular deposition of mannose-binding lectin in human glomerulonephritis. Nephrol Dial Transplant. Apr. 1999;14(4):881-6.

Lhotta et al., Membranous nephropathy in a patient with hereditary complete complement C4 deficiency. Nephrol Dial Transplant. Apr. 2004;19(4):990-3.

Linder et al., Activation of complement by cytoskeletal intermediate filaments. Nature. Mar. 8, 1979;278(5700):176-8.

Linder et al., Activation of complement by intermediate filaments of glomerular epithelial cells. Clin Immunol Immunopathol. Aug. 1986;40(2):265-75.

Linder et al., Antibody-independent binding of Clq and activation of serum complement by human skin in vitro. J Invest Dermatol. Feb. 1982;78(2):116-20.

Linder, Binding of Clq and complement activation by vascular endothelium. J Immunol. Feb. 1981;126(2):648-58.

Locht et al., Reactive arthritis and serum levels of mannose binding lectin—lack of association. Clin Exp Immunol. Jan. 2003;131(1):169-73.

MacCallum et al., Antibody-antigen interactions: contact analysis and binding site topography. J Mol Biol. Oct. 11, 1996;262(5):732-45.

Madsen et al., Association of mannose-binding-lectin deficiency with severe atherosclerosis. Lancet. Sep. 19, 1998;352(9132):959-60.

Madsen et al., Interplay between promoter and structural gene variants control basal serum level of mannan-binding protein. J Immunol. Sep. 15, 1999;155(6):3013-20.

Malhotra et al., Glycosylation changes of IgG associated with rheumatoid arthritis can activate complement via the mannose-binding protein. Nat Med. Mar. 1995;1(3):237-43.

Matsuda et al., Involvement of Mannan Binding Protein in Incidence and Development of IgA Nephropathy. J Nephrol Assoc Japan. 1997;39(3):235. Japanese.

Matsushita et al., Activation of the lectin complement pathway by H-ficolin (Hakata antigen). J Immunol. Apr. 1, 2002;168(7):3502-6.

Matsushita et al., Cutting edge: complement-activating complex of ficolin and mannose-binding lectin-associated serine protease. J Immunol. Mar. 1, 2000;164(5):2281-4.

Matsushita et al., Human mannose-binding protein is identical to a component of Ra-reactive factor. Biochem Biophys Res Commun. Mar. 16, 2000;183(2):645-51.

Mayilyan et al., Heterogeneity of MBL-MASP complexes. Mol Immunol. Mar. 2006;43(8):1286-92. Epub Aug. 15, 2005.

Miller et al., Ligand binding to proteins: the binding landscape model. Protein Sci. Oct. 1997;6(10):2166-79.

MøLLER-Kristensen et al., Levels of mannan-binding lectin-associated serine protease-2 in healthy individuals. J Immunol Methods. Nov. 2003;282(1 -2): 159-67.

Monnet et al., Synthetic peptides derived from the variable regions of an anti-CD4 monoclonal antibody bind to CD4 and inhibit HIV-1 promoter activation in virus-infected cells. J Biol Chem. Feb. 5, 1999;274(6):3789-96.

Montalto et al., A keratin peptide inhibits mannose-binding lectin. J Immunol. Mar. 15, 2001;166(6):4148-53.

Montalto et al., A peptide mimic of N-acetyl-D-glucosamine inhibits the lectin complement pathway following endothelial oxidative stress. FASEB J. 2001; 15:A339. Abstract Only.

Montalto et al., Role for complement in mediating intestinal nitric oxide synthase-2 and superoxide dismutase expression. Am J Physiol Gastrointest Liver Physiol. Jul. 2003;285(1):G197-206. Epub Mar. 13, 2003

Neth et al., Deficiency of mannose-binding lectin and burden of infection in children with malignancy: a prospective study. Lancet. Aug. 25, 2001;358(9282):614-8.

Østergaard et al., Complement activation and diabetic vascular complications. Clin Chim Acta. Nov. 2005;361(1-2):10-9.

Owens et al., The genetic engineering of monoclonal antibodies. J Immunol Methods. Feb. 10, 1994;168(2):149-65.

Petersen et al., An assay for the mannan-binding lectin pathway of complement activation. J Immunol Methods. Nov. 1, 2001;257(1-2):107-16.

Petersen et al., Control of the classical and the MBL pathway of complement activation. Mol Immunol. Oct. 2000;37(14):803-11.

Proctor et al., Comparative anti-inflammatory activities of antagonists to C3a and C5a receptors in a rat model of intestinal ischaemia/reperfusion injury. Br J Pharmacol. Jun. 2004;142(4):756-64. Epub May 24, 2004.

Reis et al., Clinical aspects and molecular basis of primary deficiencies of complement component C3 and its regulatory proteins factor I and factor H. Scand J Immunol. Mar. 2006;63(3):155-68.

Rieben et al., Immunoglobulin M-enriched human intravenous immunoglobulin prevents complement activation in vitro and in vivo in a rat model of acute inflammation. Blood. Feb. 1, 1999;93(3):942-51.

Riedemann et al., Complement in ischemia reperfusion injury. Am J Pathol. Feb. 2003;162(2):363-7.

Roos et al., Functional characterization of the lectin pathway of complement in human serum. Mol Immunol. Jan. 2003;39(11):655-68.

Roos et al., Human IgA activates the complement system via the mannan-binding lectin pathway. J Immunol. Sep. 1, 2001;167(5):2861-8.

Roos et al., Therapeutic inhibition of the early phase of complement activation. Immunobiology. Sep. 2002;205(4-5):595-609. Review.

Rossi et al., Functional characterization of complement proteases C1s/mannan-binding lectin-associated serine protease-2 (MASP-2) chimeras reveals the higher C4 recognition efficacy of the MASP-2 complement control protein modules. J Biol Chem. Dec. 23, 2005;280(51):41811-8. Epub Oct. 14, 2005.

Rossi et al., Substrate specificities of recombinant mannan-binding lectin-associated serine proteases-1 and -2. J Biol Chem. Nov. 2, 2001;276(44):40880-7. Epub Aug. 29, 2001.

Rudikoff et al., Single amino acid substitution altering antigen-binding specificity. Proc Natl Acad Sci U S A. Mar. 1982;79(6):1979-83.

Russell et al., Anti-inflammatory activity of human IgA antibodies and their Fab alpha fragments: inhibition of IgG-mediated complement activation. Eur J Immunol. Dec. 1989;19(12):2243-9.

Saevarsdottir et al., Mannan binding lectin as an adjunct to risk assessment for myocardial infarction in individuals with enhanced risk. J Exp Med. Jan. 3, 2005;201(1):117-25. Epub Dec. 28, 2004.

Sanz-Aparicio et al., The crystal structure of Canavalia brasiliensis lectin suggests a correlation between its quaternary conformation and its distinct biological properties from Concanavalin A. FEBS Lett. Mar. 17, 1997;405(1):114-8.

Sato et al., Molecular characterization of a novel serine protease involved in activation of the complement system by mannose-binding protein. Int Immunol. Apr. 1994;6(4):665-9.

Satoh et al., Midzonal necrosis of the liver after concanavalin A-injection. Tohoku J Exp Med. Oct. 1996;180(2):139-52.

Seelen et al., Functional analysis of the classical, alternative, and MBL pathways of the complement system: standardization and validation of a simple ELISA. J Immunol Methods. Jan. 2005;296(1-2):187-98. Epub Dec. 15, 2004.

Selander et al., Mannan-binding lectin activates C3 and the alternative complement pathway without involvement of C2. J Clin Invest. May 2006;116(5):1425-34.

Shikhman et al., Cytokeratin Peptide SFGSGFGGGY Mimics N-Acetyl-β-D-Glucosamine in Reaction with Antibodies and Lectins, and Induces In Vivo and Anti-Carbohydrate Antibody Response. J Immunol. 1994:5593-606.

Sjoholm et al., Complement deficiency and disease: an update. Mol Immunol. Jan. 2006;43(1-2):78-85.

Souza et al., APT070 (Mirococept), a membrane-localised complement inhibitor, inhibits inflammatory responses that follow intestinal ischaemia and reperfusion injury. Br J Pharmacol. Aug. 2005;145(8):1027-34.

Stahl et al., Reperfusion injury in surgery. Role of the endothelium, oxidative stress and complement activation (Invited review). New Surgery. 2001; 1:62-6.

Stahl et al., Role for the alternative complement pathway in ischemia/reperfusion injury. Am J Pathol. Feb. 2003;162(2):449-55.

Stahl, The Immune System—Complementary Medicine. The Economist. May 13, 2003; 26-7.

Stanworth et al., Absence of an association between mannose-binding lectin polymorphism and rheumatoid arthritis. Br J Rheumatol. Feb. 1998;37(2):186-8.

Steffensen et al., Detection of structural gene mutations and promoter polymorphisms in the mannan-binding lectin (MBL) gene by polymerase chain reaction with sequence-specific primers. J Immunol Methods. Jul. 31, 2000;241(1-2):33-42.

Super et al., The level of mannan-binding protein regulates the binding of complement-derived opsonins to mannan and zymosan at low serum concentrations. Clin Exp Immunol. 1990;79:144-150.

Suzuki et al., Membranoproliferative glomerulonephritis associated with hereditary deficiency of the 4th component of complement. Clin Nephrol. Oct. 2003;60(4):279-83.

Szebeni et al., Hemodynamic changes induced by liposomes and liposome-encapsulated hemoglobin in pigs: a model for pseudoallergic cardiopulmonary reactions to liposomes. Role of complement and inhibition by soluble CR1 and anti-C5a antibody. Circulation. May 4, 1999;99(17):2302-9.

Szebeni et al., Liposome-induced pulmonary hypertension: properties and mechanism of a complement-mediated pseudoallergic reaction. Am J Physiol Heart Circ Physiol. Sep. 2000;279(3):H1319-28.

Szeplaki et al., Elevated complement C3 is associated with early restenosis after eversion carotid endarterectomy. Thromb Haemost. Oct. 2006;96(4):529-34.

Takahashi et al., A truncated form of mannose-binding lectin-associated serine protease (MASP)-2 expressed by alternative polyadenylation is a component of the lectin complement pathway. Int Immunol. May 1999;11(5):859-63.

Takahashi et al., Association of mannose binding lectin (MBL) gene polymorphism and serum MBL concentration with characteristics and progression of systemic lupus erythematosus. Ann Rheum Dis. Feb. 2005;64(2):311-4.

Takahashi et al., Lack of mannose-binding lectin-A enhances survival in a mouse model of acute septic peritonitis. Microbes Infect. Jul. 2005;4(8):773-84.

Tan et al., Improvements on the purification of mannan-binding lectin and demonstration of its Ca(2+)-independent association with a C1s-like serine protease. Biochem J. Oct. 15, 2006;319 (Pt 2):329-32.

Teillet et al., The two major oligomeric forms of human mannan-binding lectin: chemical characterization, carbohydrate-binding properties, and interaction with MBL-associated serine proteases. J Immunol. Mar. 1, 2005;174(5):2870-7.

Tenner et al., Mannose Binding Protein (MBP) Enhances Mononuclear Phagocyte Function via a Receptor that Contains the 126,000 $M_r$ Component of the C1q Receptors. Immunity. 1995;3(4):485-93.

Terai et al., α2-Macroglobulin binds to and inhibits mannose-binding protein-associated serine protease. Intl Immunol. 1995;7(10):1579-84.

Terai et al., Human serum mannose-binding lectin (MBL)-associated serine protease-1 (MASP-1): determination of levels in body fluids and identification of two forms in serum. Clin Exp Immunol. 1997;110:317-23.

Terai et al., Relationship between gene polymorphisms of mannose-binding lectin (MBL) and two molecular forms of MBL. Eur J Immunol. Oct. 2003;33(10):2755-63.

Thiel et al., A second serine protease associated with mannan-binding lectin that activates complement. Nature. Apr. 3, 1997;386(6624):506-10.

Thiel et al., Assays for the functional activity of the mannan-binding lectin pathway of complement activation. Immunobiology. Sep. 2002;205(4-5):446-54.

Thiel et al., The concentration of the C-type lectin, mannan-binding protein, in human plasma increases during an acute phase response. Clin Exp Immunol. Oct. 1992;90(1):31-5.

Tofukuji et al., Anti-C5a monoclonal antibody reduces cardiopulmonary bypass and cardioplegia-induced coronary endothelial dysfunction. J Thorac Cardiovasc Surg. Dec. 1998;116(6):1060-8.

Turner et al., The lectin pathway of complement activation. Res Immunol. Feb. 1996;147(2):110-5. Review.

Turner, Mannose-binding lectin: the pluripotent molecule of the innate immune system. Immunol Today. Nov. 1996;17(11):532-40. Review.

Väkevä et al., Myocardial infarction and apoptosis after myocardial ischemia and reperfusion: role of the terminal complement components and inhibition by anti-C5 therapy. Circulation. Jun. 9, 1998;97(22):2259-67.

Väkevä et al., Reoxygenation of hypoxic human umbilical vein endothelial cells (HUVECs) activates complement and induces apoptosis. Role of C5b-9. Exp Clin Immunogenet. 1997;14:108. Abstract Only.

Valdimarsson et al., Reconstitution of opsonizing activity by infusion of mannan-binding lectin (MBL) to MBL-deficient humans. Scand J Immunol. Aug. 1998;48(2):116-23.

Verma et al., Clinical significance of mannose-binding lectin-associated serine protease-2 expression in esophageal squamous cell carcinoma. Int J Cancer. Jun. 15, 2006;118(12):2930-5.

Vorup-Jenson et al., MASP-2, the C3 convertase generating protease of the MBLectin complement activating pathway. Immunobiology. Aug. 1998;199(2):348-57. Review.

Wada et al, Inhibition of complement C5 reduces local and remote organ injury after intestinal ischemia/reperfusion in the rat. Gastroenterology. Jan. 2001;120(1):126-33.

Wallis et al., Localization of the serine protease-binding sites in the collagen-like domain of mannose-binding protein: indirect effects of naturally occurring mutations on protease binding and activation. J Biol Chem. Apr. 2, 2004;279(14):14065-73. Epub Jan. 14, 2004.

Walport, Complement. First of two parts. N Engl J Med. Apr. 5, 2001;344(14):1058-66.

Walport, Complement. Second of two parts. N Engl J Med. Apr. 12, 2001;344(15):1140-4.

Walsh et al., Chapter 19. Role of complement in myocardial ischemia and infarction. In: Szebeni J, editor. The Complement System. Novel Roles in Health and Disease. Kluwer Academic Publishers. Massachusetts, Jun. 2004. 421-35.

Walsh et al., Fluorochrome-linked immunoassay for functional analysis of the mannose binding lectin complement pathway to the level of C3 cleavage. J Immunol Methods. 2007 Jun. 30;323(2):147-59. Epub May 11, 2007.

Walsh et al., Mannose-binding lectin is a regulator of inflammation that accompanies myocardial ischemia and reperfusion injury. J Immunol. Jul. 1, 2005;175(1):541-6.

Walsh et al., Myocardial Ischemia-reperfusion injury is dependent on lectin complement activation. American College of Cardiology. Mar. 10, 2004; 11:15am-11:30am. Presentation No. 883-4. Abstract Only.

Weisman et al., Recombinant soluble CR1 suppressed complement activation, inflammation, and necrosis associated with reperfusion of ischemic myocardium. Trans Assoc Am Physicians. 1990;103:64-72.

Williams et al., Intestinal reperfusion injury is mediated by IgM and complement. J Appl Physiol. Mar. 1999;86(3):938-42.

Windsor et al., Tumor necrosis factor-alpha blockade prevents neutrophil CD18 receptor upregulation and attenuates acute lung injury in porcine sepsis without inhibition of neutrophil oxygen radical generation. J Clin Invest. Apr. 1993;91(4):1459-68.

Yang et al., Complete complement components C4A and C4B deficiencies in human kidney diseases and systemic lupus erythematosus. J Immunol. Aug. 15, 2004;173(4):2803-14.

Ytting et al., Increased activity of the mannan-binding lectin complement activation pathway in patients with colorectal cancer. Scand J Gastroenterol. Jul. 2004;39(7):674-9.

Ytting et al., Preoperative mannan-binding lectin pathway and prognosis in colorectal cancer. Cancer Immunol Immunother. Mar. 2005;54(3):265-72. Epub Sep. 21, 2004.

Ytting et al., Serum mannan-binding lectin-associated serine protease 2 levels in colorectal cancer: relation to recurrence and mortality. Clin Cancer Res. Feb. 15, 2005;11(4):1441-6.

Zhang et al., Association between mannose-binding lectin gene polymorphisms and susceptibility to severe acute respiratory syndrome coronavirus infection. J Infect Dis. Oct. 15, 2005;192(8):1355-61. Epub Sep. 8, 2005.

Zhao et al., Anoxia and reoxygenation of human endothelial cells decrease ceramide glucosyltransferase expression and activates caspases. Faseb J. Apr. 2003;17(6):723-4. Epub Feb. 5, 2003.

Zhao et al., Identification of human mannose binding lectin (MBL) recognition sites for novel inhibitory antibodies. Hybridoma and Hybridomics. Feb. 2002;21(1):25-36.

Zhao et al., Murine model of gastrointestinal ischemia associated with complement-dependent injury. J Appl Physiol. Jul. 2002;93(1):338-45.

m

* cited by examiner

US 8,524,453 B2

LECTIN COMPLEMENT PATHWAY ASSAYS AND RELATED COMPOSITIONS AND METHODS

RELATED APPLICATIONS

This application is a national stage filing under 35 U.S.C §371 of International Application No. PCT/US2007/003644, filed Feb. 9, 2007, now published as WO 2007/095154 A2, which claims priority under 35 U.S.C. §119 from U.S. provisional application Ser. No. 60/771,880, filed Feb. 10, 2006. The entire contents of which is herein incorporated by reference.

GOVERNMENT SUPPORT

Aspects of the invention may have been made using funding from National Institutes of Health Grant number HL52886, HL56086, DE017821 and/or HL79758. Accordingly, the government may have rights in the invention.

FIELD OF THE INVENTION

This invention is related, in part, to assays for analyzing the lectin complement pathway (LCP) as well as to compositions and methods related thereto.

BACKGROUND OF THE INVENTION

Clinically, mannose binding lectin (MBL) moderates disease severity in both its 'traditional' and 'non-traditional' capacities. In it's 'traditional' role, MRL deficiencies have been linked to recurrent respiratory infections (Cedzynski et al., 2004; Gomi et al., 2004; Zhang et al., 2005; Kaur et al., 2006), meningococcal disease (van Emmerik et al., 1994; Bax et al., 1999; Kuipers et al., 2003; Bathum et al., 2006), and P. aeruginosa infection in burn patients (Moller-Kristensen et al., 2006). Alternatively, MBL recognition of self-antigens has been demonstrated in sterile inflammatory processes including systemic lupus erythematosus (Ohlenscfilaeger et al., 2004; Seelen et al., 2005b; Calvo-Alen et al., 2006; Font et al., 2006), thoracoabdominal aortic aneurysm repair (Fiane et al., 2003), IgA nephritis (Endo et al., 1998; Roos et al., 2001; Hisano et al., 2001; Roos et al., 2006), rheumatoid arthritis (Garred et al., 2000; Saevarsdottir et al., 2001; Gupta et al., 2005; Burton and Dwek, 2006), atherosclerosis (Madsen et al., 1998; Hegele et al., 2000; Spence and Norris, 2003; Sjoholm et al., 2006), diabetes (Hansen et al., 2003; Hansen et al., 2004; Bouwman et al., 2005; Hovind et al., 2005), cancer (Baccarelli et al., 2006; Scudiero et al., 2006) and coronary artery disease (Best et al., 2004; Saevarsdottir et al., 2005). The dichotomous nature of this C-type lectin to recognize both foreign- and/or self-antigens under varying conditions is the focus of intense research, as the appropriate balance of functional MBL and LCP activation may predict outcomes in various disease states.

Several assays are available for the quantification of MBL, either functionally (mannan assay) or non-functionally (sandwich ELISA) (Petersen et al., 2001; Thiel et al., 2002; Roos et al., 2003; Takahashi et al., 2005; Seelen et al., 2005a). However, these assays cannot fully investigate the functional status of the early lectin pathway cascade proteins in a single analysis. Further, activation of the alternative complement pathway directly via MBL (e.g., in the absence of MASP-2) can not be assessed by available assays.

SUMMARY OF THE INVENTION

Provided herein are methods for assessing LCP activation by measuring one or more LCP components in a sample, such as a biological sample. Also provided herein are compositions and other methods related thereto.

In one aspect; the method comprises measuring MBL in a biological sample, measuring another LCP component in the biological sample, and assessing LCP activation in the biological sample. In one embodiment, the method further comprises removing non-covalently bound MBL/MASP-2 complexes. In another embodiment, the other LCP component is MASP-2, C3 or C4. In a further embodiment, the method further comprises measuring a further LCP component in the biological sample. In still another embodiment, the further LCP component is MASP-2, C3 or C4. In yet another embodiment, the other LCP component is C4 and the further LCP component is C3. In still a further embodiment, still another LCP component is measured in the biological sample. In one embodiment, the still other LCP component is MASP-2. In one embodiment, MBL, C4 and C3 are measured in the method. In a further, embodiment, MBL MASP-2, C4 and C3 are measured in the method.

In another aspect, a method of assessing LCP activation is provided, comprising contacting a substrate coated with a ligand of MBL with a biological sample, contacting the sample with a detectably labeled agent that specifically binds MBL, determining the amount of MBL present, and assessing LCP activation in the sample with the results. The method, in one embodiment, further comprises removing non-covalently bound MBL/MASP-2 complexes from the sample. The method, in another embodiment, further comprises contacting the sample with a detectably labeled agent that specifically binds C4. The method, in still another embodiment, further comprises contacting the sample with a detectably labeled agent that specifically binds C3. The method, in a further embodiment, comprises determining the amount of C4 and/or C3 present.

In one embodiment, the ligand of MBL is mannan, mannose or GlcNAc. In another embodiment, the agent that specifically binds MBL is an anti-MBL antibody. In a further embodiment, the agent that specifically binds C4 is an anti-C4 antibody. In yet another embodiment, the agent that specifically binds C3 is an anti-C3 antibody.

In another embodiment, the method further comprises contacting the sample with a detectably labeled agent that specifically binds MASP-2, and determining the amount of MASP-2 present. In one embodiment, the agent that specifically binds MASP-2 is an anti-MASP-2 antibody.

In still another aspect, a method for assessing LCP activation is provided wherein the biological sample contacted with the ligand-coated substrate does not contain non-covalently bound MBL/MASP-2 complexes or has had such complexes removed. The method, in one embodiment, further comprises contacting the sample with a detectably labeled agent that specifically binds C4. The method, in still another embodiment, further comprises contacting the sample with a detectably labeled agent that specifically binds C3. The method, in a further embodiment, comprises determining the amounts of C4 and/or C3 present.

In one embodiment, the ligand of MBL is mannan, mannose or GlcNAc. In another embodiment, the agent that specifically binds C4 is an anti-C4 antibody. In yet another embodiment, the agent that specifically binds C3 is an anti-C3 antibody.

In another aspect, a method for assessing LCP activation is provided that comprises a) incubating the biological sample in one or more wells of a multi-well plate, wherein the wells have been coated with a ligand of MBL (e.g., mannan), b) washing the well or wells and incubating with a composition comprising an antibody that binds specifically to MBL, which optionally is detectably labeled, and c) determining the amount of MBL present. In one embodiment, the composition of step b) further comprises an antibody that binds specifically to MASP-2, which optionally is detectably labeled, and step c) further comprises determining the amount of MASP-2 present. In another embodiment, when two antibodies are used, the labels of the antibodies are either the same or distinct/different. In one embodiment, one label is detected at 700 nm and the other at 800 nm.

In another aspect, the method further comprises d) washing the well or wells containing the sample in a buffer that can be used to remove non-covalently bound MBL/MASP-2 complexes. In one embodiment, the method further comprises e) incubating with an antibody that binds specifically to C3, which optionally is bound to a detectable label that is either the same or different from the other label(s), and f) determining the amount of C3 present. In another embodiment, step e) further comprises incubating with an antibody that binds specifically to C4, which is also optionally attached to a detectable label that is either the same or different from the other label(s) and step f) further comprises determining the amount of C4 present. In one embodiment, when the C3 and C4 antibodies are labeled the labels are distinct.

In still another aspect, a method for assessing MASP-2 function is provided. In one aspect, the method comprises measuring C4 in a biological sample, and determining MASP-2 function with the result. The method, in one embodiment, further comprises measuring another LCP component in the biological sample. In another embodiment, the other LCP component is MBL, MASP-2 or C3. In a further embodiment, the method further comprises measuring a further LCP component in the biological sample. In still another embodiment, the further LCP component is MBL, MASP-2 or C3. In still a further embodiment, still another LCP component is measured in the biological sample. In another embodiment, the method further comprises a step of removing non-covalently bound MBL/MASP-2 complexes.

In any of the methods provided herein, the measurement or detection of MBL can be replaced with the measurement or detection of a ficolin (and the ligand of MBL with a ligand of ficolin as needed) or other activator of the LCP (and ligand as appropriate). Therefore, in a further aspect, a method of assessing lectin complement pathway (LCP) activation, comprising measuring a ficolin in a biological sample, and assessing LCP activation in the biological sample is provided. In one embodiment, the method further comprises measuring another LCP component in the biological sample. In another embodiment, the other LCP component is MASP-2, C3 or C4. In still another embodiment, the method further comprises measuring a further LCP component in the biological sample. In still another embodiment, the further LCP component is MASP-2, C3 or C4. In a further embodiment, the other LCP component is C4 and the further LCP component is C3. In yet a further embodiment, still another LCP component is measured in the biological sample. In another embodiment, the still other LCP component is MASP-2. In one embodiment, the ficolin is L-, H- or M-ficolin.

In one embodiment, in methods which include a step of removing non-covalently bound MBL/MASP-2 complexes, the non-covalently bound MB ASP-2 complexes are removed with the use of a buffer that contains a calcium chelator. In another embodiment, the calcium chelator is EDTA or EGTA. In still another embodiment, the buffer further contains a competitive inhibitor of MBL. In one embodiment, the competitive inhibitor is mannose, N-acetylglucosamine (GlcNAc), fucose, glucose or an anti-MBL antibody.

In one embodiment, the biological sample is a serum, plasma or cerebrospinal fluid sample. In another embodiment, when a plasma sample is analyzed, the method can further include the step of coverting the plasma sample to a serum sample. In one embodiment, the step comprises diluting the plasma sample 1:1 with a $VBS^{++}$ buffer that is supplemented with calcium chloride. In another embodiment, the step can further comprises removing fibrin clots that develop.

In another embodiment, the biological sample is from a subject with or suspected of having a LCP-mediated disease. In another embodiment, the LCP-mediated disease is acute respiratory distress syndrome, arteriosclerosis, arthritis (e.g., rheumatoid arthritis), atherosclerosis, cancer (e.g., breast cancer, colorectal cancer, esophageal squamous cell carcinoma, lung cancer and prostate cancer), cardiopulmonary bypass, cardiovascular disease, chronic angioedema, coronary artery disease, diabetes, infection (e.g., respiratory infection, *P. aeruginosa* infection, sepsis (e.g., in burn patients)), autoimmune disease, lupus (e.g., SLE), meningococcal disease, myocardial infarction, *Neisseria* menningitis, nephritis (e.g., IGA nephritis and membranoproliferative glomerulonephritis), neurological disease, neuropathic pain or stroke. In another embodiment, the subject is one that has undergone or is undergoing dialysis. In a further embodiment, the subject is one in which thoracoabdominal aortic aneurysm repair is occurring or has occurred. In still another embodiment, the subject is one that has undergone transplantation. In yet another embodiment, the subject is one in which ischemia and reperfusion has occurred or is occurring. In one embodiment, the ischemia and reperfusion is gastrointestinal ischemia and reperfusion. In a further embodiment, the subject has ischemic heart disease.

The methods, in one embodiment, are performed with the same biological sample or portion thereof. In another embodiment, the methods are performed in the same area of a substrate to which the sample is contacted. In one embodiment, therefore, the methods are performed in the same well of a well plate.

The methods provided, in one embodiment, are performed with a sample size of less than 500 µl. In another embodiment, the sample size is less than 400 µl, 300 µl, 200 µl, 100 µl or 50 µl. In yet another embodiment, the sample size is 1-20 µl. In a further embodiment, the sample size is 15-20 µl, 10-15 µl, 5-10 µl or 1-5 µl.

In another aspect, kits are provided that can be used to carry out the methods of the invention. In one aspect, a kit is provided comprising an agent that specifically binds MBL, a buffer comprising a calcium chelator, an agent that specifically binds another LCP component, and instructions for assessing LCP activation. In one embodiment, the buffer further comprises a competitive inhibitor of MBL. In another embodiment, the other LCP component is MASP-2, C3 or C4. In a further embodiment, the kit further comprises an agent that specifically binds a further LCP component. In one embodiment, the further LCP component is MASP-2, C3 or C4. In another embodiment, the other LCP component is C4 and the further LCP component is C3. In a further embodiment, the agents that specifically bind are antibodies.

For any of the kits provided herein that include an agent that specifically binds MBL, an agent that specifically binds a ficolin (or other activator of LCP) can be substituted in its place. In another aspect, a kit is provided comprising an agent that specifically binds a ficolin, an agent that specifically binds another LCP component, and instructions for assessing LCP activation. In one embodiment, the other LCP component is MASP-2, C3 or C4. In another embodiment, the kit further comprises an agent that specifically binds a further LCP component. In a further embodiment, the further LCP component is MASP-2, C3 or C4. In yet another embodiment, the other LCP component is C4 and the further LCP component is C3. In one embodiment, the agents that specifically bind are antibodies. In another embodiment, the ficolin is an L-, H- or M-ficolin.

In still another aspect, a kit is provided that comprises a buffer comprising a calcium chelator, an agent that specifically binds C4, and instructions for assessing MASP-2 activation. In one embodiment, the buffer further comprises a competitive inhibitor of MBL.

In another embodiment, the kit further comprises an agent that specifically binds another LCP component. In a further embodiment, the other LCP component is MBL, MASP-2 or C3. In one embodiment, the agent that specifically binds is an antibody. In another embodiment, the agents that specifically bind are antibodies.

In still another aspect, buffer compositions that can be used for removing non-covalently bound MBL/MASP-2 complexes are provided. In one aspect, a buffer composition comprising a calcium chelator and a competitive inhibitor of MBL is provided. In one embodiment, the competitive inhibitor of MBL is mannose, N-acetylglucosamine (GlcNAc), fucose, glucose or an anti-MBL antibody. In another embodiment, the competitive inhibitor is mannose. In still another embodiment, the competitive inhibitor is present at a concentration of at least 30 mM. In a further embodiment, the competitive inhibitor is present at a concentration of 30 mM-300 mM. In yet another embodiment, the calcium chelator is. EDTA or EGTA. In still another embodiment, the calcium chelator is present at a concentration of greater than or equal to 10 mM. In yet a further embodiment, the calcium chelator is present at a concentration of 10 mM-100 mM. In another embodiment, the buffer composition has a pH of 7-8. In a further embodiment, the buffer composition has a pH of 7.4-7.8. In one embodiment, the buffer composition comprises 50 mM Tris-HCl, 150 mM NaCl, 10 mM EDTA, 0.05% Tween-20, 100 mM D(+)-mannose and has a pH 7.8.

Each of the limitations of the invention can encompass various embodiments of the invention. It is, therefore, anticipated that each of the limitations of the invention involving any one element or combinations of elements can be included in each aspect of the invention.

DETAILED DESCRIPTION OF THE INVENTION

The humoral response to invading pathogens is mediated by a repertoire of innate immune molecules and receptors able to recognize pathogen-associated molecular patterns (PAMPs). Mannose binding lectin and ficolins, initiation molecules of the lectin complement pathway (LCP), are members of a family of acute phase proteins bridging innate and adaptive immunity. It has become clear that early components of the MBL-dependent LCP also recognize self-antigens and/or IgM following oxidative stress. The concentration of human MBL is determined by the MBL2 gene, which has several haplotypes that determine circulating MBL level and function. Further, evidence suggests direct activation of the alternative complement pathway, independent of the serine protease MASP-2, through an MBL-mediated association. Current assays for MRI, and MASP-2 lack the ability to assess all components of the early LCP in a single assay system to the level of C3 cleavage (e.g., the step needed for opsonization of pathogens). Further, the available assays do not assess the functional state of MBL, MASP-2 as well as the C3 convertase. Therefore, assays have been developed such as a low volume, fluorochrome linked immunoassay (FLISA) that quantitatively assess the functional status of MBL, MASP-2 and C3 convertase. The FLISA can be used, for example, as a high-throughput assay to identify potential deficiencies in the MBL-dependent LCP, as well as to identify specific human disease correlations between these components and clinical outcomes.

Figure 1:
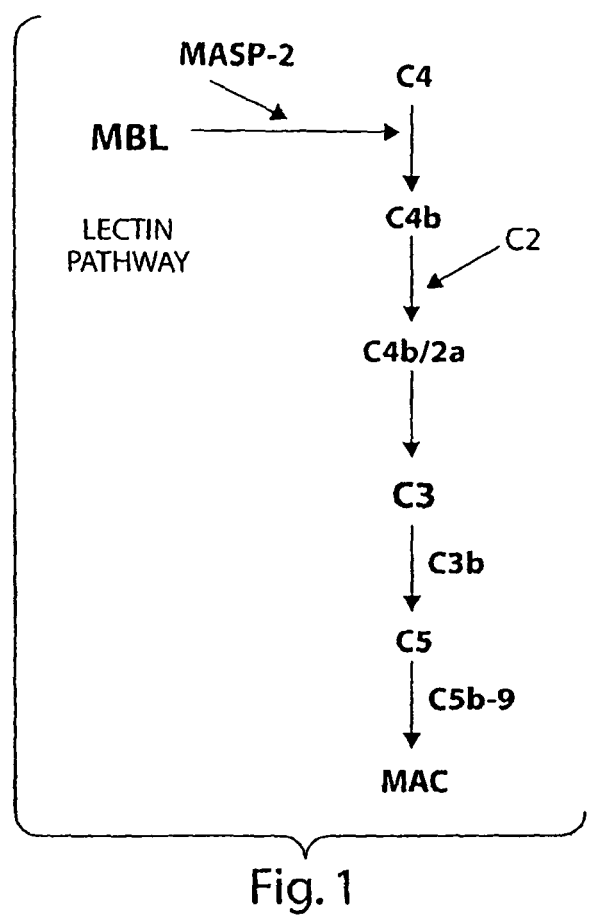
FIG. 1 provides an outline of important steps of the LCP.
Figure 5:
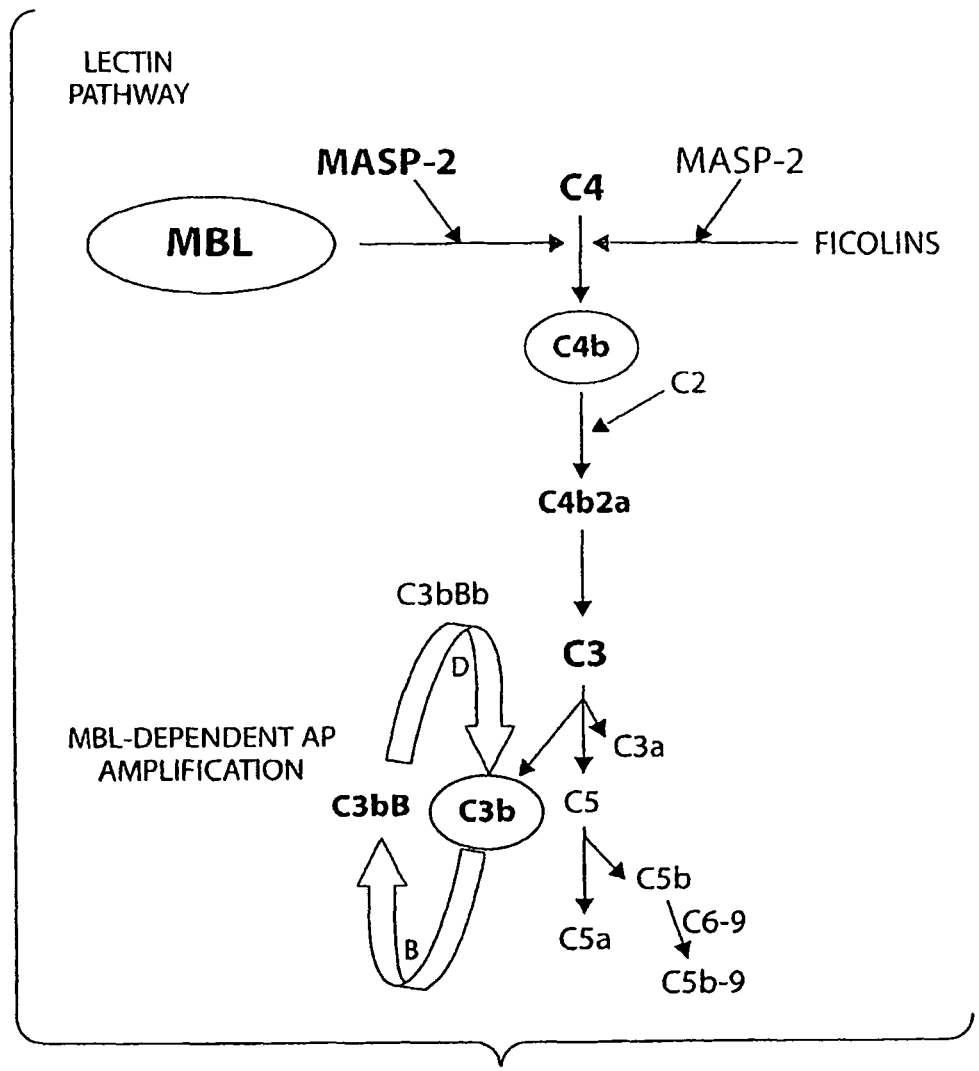
FIG. 5 demonstrates the key components in LCP activation that can be analyzed using LCP FLISA. Oval outlines delineate the endpoints directly analyzed by the assay.

Provided herein are methods that allow for the assessment of LCP activation in a biological sample. The assays include the measurement of one or more LCP components in a biological sample. A "LCP component" can be any of the components provided in FIGS. 1 and 5. Such components include, for example, MBL, MASP-2, C4, C3, ficolins (such as L-, H- and M-ficolins), etc. The components also include complexes or breakdown products formed at any step of the pathway, such complexes and breakdown products are also illustrated in FIGS. 1 and 5.

In one embodiment, the methods include the steps of measuring MBL or a ficolin (e.g., L-, H- or M-ficolin) in a biological sample as well as measuring at least one other LCP component in the biological sample. The results from the steps can be used to assess LCP activation. The assessment of LCP activation is the determination of whether or not the LCP is active and/or the determination of the level of activation. The assessment of LCP activation can also refer to the function or activation of various LCP components within the pathway. Therefore, the assessment of LCP activation can also include the assessment of the pathway up to C3 cleavage, the assessment of C3 convertase or the function of MASP-2 (such as through the measurement of C4). "Measuring" or "measurement", when used in regard to an LCP component, is intended to refer to any assessment of the amount of a particular LCP component, in a sample. "Amount" is intended to include a determination of the presence or absence of the LCP component as well as the level of the LCP component in the sample. The "level" is some quantitation of the LCP component in the sample and can be a relative value or an absolute value. Such measuring or measurement can be accomplished with any means known in the art or provided herein. Quantitation can be performed with methods known in the art and those provided herein, such as in the Examples. In one embodiment, quantitation is performed using standard curves for the LCP component(s) detected.

The measurement of a LCP component, such as MBL, can be performed with any of a number of methods well known in the art. For example, the LCP component can be measured using an agent that specifically binds the LCP component. The agent can then be detected. Detection of binding of the agent to the LCP component can be accomplished, for example, by detecting a label bound to the agent or to a molecule that binds thereto. In some embodiments, the agent is an antibody and the antibody is detectably labeled. In this embodiment, it is the label bound to the antibody agent that is detected to measure the LCP component. In other embodiments, the agent is an antibody and a molecule that binds the agent is detectably labeled. The LCP component, in this embodiment is, therefore, measured by detecting the label bound to the molecule that binds the antibody. This molecule can, in some embodiments, also be an antibody.

The other LCP component can be any of the LCP components as described above. In one embodiment, where MBL or a ficolin is measured, the other LCP component can be MASP-2. In another embodiment, the other LCP component can be C3 or C4. In still another embodiment, C3 and C4 can be measured. In a further embodiment, all four of MBL (or a ficolin), MASP-2, C3 and C4 are measured. In still another embodiment, MBL (or a ficolin), C3 and C4 are measured in order to assess LCP activation.

Methods are also provided where the function of MASP-2 is assessed. Such methods can include the step of measuring C4. In some embodiments, the methods can also include the measurement of another LCP component. Such components have been provided elsewhere herein.

The assays can be performed on any substrate. Substrates include well plates, such as 96 or 384 well plates. In some embodiments, the assay is performed in a single area of the substrate, such as a single well of a well plate. In such embodiments, all of the LCP components that are measured are measured with assay steps within the same well. In other embodiments, one or more LCP components are measured in one well and one or more other LCP components are measured in another well. For example, MBL (or a ficolin), or MBL and MASP-2 can be measured with binding agents that specifically bind thereto in one well and other LCP components, such as C3 and/or C4, can be measured in another well. Replicate samples can be measured with other substrates, or in other areas of the same substrate, such as other wells of the same assay plate, as can one or more control samples. In methods where MBL or ficolin is measured, the substrate can be coated with a ligand of MBL or ficolin. Such ligands are known in the art and include MBL ligands such as mannan, mannose or N-acetylglucosamine (GlcNAc). Ligands for ficolin include GlcNAc. Other ligands for MBL and ficolin are known to those of ordinary skill in the art.

The assays, in some embodiments, are performed with the same biological sample or same portion of the biological sample. Alternatively, steps of the assays can be performed with more than one biological sample or more than one portion of a biological sample. The assays, in other embodiments, can be performed with a small amount of sample. In some embodiments, the sample size is less than 500 µl, 400 µl, 300 µl, 200 µl, 100 µl or 50 µl. In still another embodiment, the sample size is 15-100 µl. In yet another embodiment, the sample size is 1-20 µl. In a further embodiment, the sample size is 15-20 µl, 10-15 µl, 5-10 µl or 1-5 µl.

In some embodiments, one or more of the LCP components (such as MBL, ficolin or MASP-2) can be removed prior to performing the rest of the steps of a method for assessing LCP activation. For example, in some embodiments where LCP activation via ficolin measurement is desired, MBL can be removed from the biological sample. In other embodiments, where LCP activation via MBL measurement is desired, ficolins can be removed. Techniques for removing a LCP component are known to those of ordinary skill in the art. For example, centrifugation is used, or antibodies directed to the LCP component are used and the sample processed using chromatography.

Any of the methods provided can further include the step of removing non-covalently bound complexes, such as MBL/MASP-2 complexes, from the sample. Non-covalently bound complexes, such as MBL/MASP-2 complexes, can be removed with the use of a buffer that includes a calcium chelator, such as EDTA or EGTA. Other chelators will be apparent to those of ordinary skill in the art. The chelators can be present, in some embodiments, in the buffer composition at a concentration of greater than or equal to 10 mM. In other embodiments, the chelator is present at a concentration of between 10-100 mM, such as 20 mM, 30 mM, 40 mM, 50 mM, 60 mM, 70 mM, 80 mM, 90 mM or 100 mM. The buffers can also include a competitive inhibitor, such as a competitive inhibitor of MBL. "Competitive inhibitors of MBL" include mannose, GlcNAc, fucose, glucose or an agent that specifically binds MBL, such as an anti-MBL antibody. Other competitive inhibitors are known to those of ordinary skill in the art. The competitive inhibitor can be present, in some embodiments, at a concentration of at least 30 mM. In other embodiments the competitive inhibitor is present at a concentration of 30-300 mM, such as 40 mM, 50 mM, 60 mM, 70 mM, 80 mM, 90 mM, 100 mM, 150 mM, 200 mM, 250 mM or 300 mM. The buffer compositions can, in some embodiments, have a pH of 7-8. In other embodiments, the buffer has a pH of 7.4-7.8, such as 7.4, 7.5, 7.6, 7.7 or 7.8. In one embodiment, the buffer contains 50 mM Tris-HCl, 150 mM NaCl, 10 mM EDTA, 0.05% Tween-20, 100 mM D(+)-mannose and has a pH 7.8. Compositions comprising the buffers described herein are also provided.

The assays can, in some embodiments, include washing, mixing and stirring steps as necessary or as otherwise described herein, particularly in the Examples. Including such steps in any of the methods provided herein is well within the routine knowledge of one of ordinary skill in the art.

The assays/methods provided can be used with any of a number of detection systems, in addition to the Odyssey Infrared Imaging System (LICOR) or Aerius detection systems, and one of ordinary skill in the art can make appropriate simple and routine modifications as necessary. Any modifications that may be needed (e.g., with the use of enzyme linked antibodies or other fluorescent antibodies), depending on the detection system used, are well within the ordinary skill of those in the art. Other examples of detection systems include fluorescent plate readers, luminometers, spectrophotometer plate readers, etc. One of ordinary skill in the art will readily understand how to perform the assays/methods provided using any of these detector systems as well as others known in the art. Optionally, the detector systems can be coupled to a liquid handling system and/or an automatic plate washer such that numerous samples can be easily and quickly analyzed. The assays provided herein can be, therefore, performed in a high throughput format.

The measurement of an LCP component (e.g., MBL) can be accomplished using an agent that specifically binds to the LCP component. Agents that specifically bind MBL include those that specifically bind MB; when not complexed to MASP-2 as well as those that specifically bind to MBL when complexed with MASP-2. Agents that specifically bind MASP-2 include those that specifically bind MASP-2 when not complexed to MBL as well as those that specifically bind to MASP-2 when complexed with MBL. Agents that specifically bind to C3 include those that bind C3, C3b or some other cleavage product thereof. Agents that specifically bind to C4 include those that bind C4, C4b or to some other cleavage product thereof. Such agents can also include those that bind a complex that includes C4 or a portion thereof, such as the C4b2a complex.

An "agent that specifically binds" is any molecule that binds with a greater affinity to the molecule of interest than to some other molecule (in some embodiments, an unrelated molecule). Typically, the agent binds with an affinity that is at least two-fold greater than its affinity for binding to other molecules. In some embodiments, the agents can bind with an avidity and/or binding affinity that is 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 7-fold, 10-fold, 20-fold, 30-fold, 40-fold, 50-fold, 70-fold, 100-fold, 200-fold, 300-fold, 500-fold, 1000-fold or more than that exhibited by binding to another molecule.

The agents that specifically bind can be binding peptides, such as antibodies or antigen binding fragments thereof. The binding peptides, in some embodiments, can be isolated. As used herein, the term "isolated" means that the agents are substantially pure and are essentially free of other substances with which they may be found, for example, in nature or in vivo systems to an extent practical and appropriate for their intended use. In particular, the agents are sufficiently pure and are sufficiently free from other constituents, such as, in the case of binding peptides, biological constituents of their hosts cells so as to be useful in, for example, the assays/methods provided herein. Because an agent may be admixed with a pharmaceutically acceptable carrier in a pharmaceutical preparation, the agent may comprise only a small percentage by weight of the preparation. The agent is nonetheless substantially pure in that it has been substantially separated from the substances with which it may be associated, for example, in living systems.

Binding peptides may be synthesized or produced by recombinant means by those of skill in the art. Methods for preparing or identifying peptides which bind to a particular target are well known in the art. Molecular imprinting, for instance, may be used for the de novo construction of macromolecular structures such as peptides which bind to a particular molecule. See, for example, Kenneth J. Shea, Molecular Imprinting of Synthetic Network Polymers: The De Novo synthesis of Macromolecular Binding and Catalytic Sites, *TRIP* Vol. 2, No. 5, May 1994; Klaus Mosbach, Molecular Imprinting, *Trends in Biochem. Sci.*, 19(9) January 1994; and Wulff, G., in Polymeric Reagents and Catalysts (Ford, W. T., Ed.) *ACS Symposium* Series No. 308, pp 1.86-230, *American Chemical Society* (1986). One method for preparing mimics of binding peptides involves the steps of: (i) polymerization of functional monomers around a known binding peptide or the binding region of an antibody (the template) that exhibits a desired activity; (ii) removal of the template molecule; and then (iii) polymerization of a second class of monomers in the void left by the template, to provide a new molecule which exhibits one or more desired properties which are similar to that of the template. In addition to preparing peptides in this manner other binding molecules, such as polysaccharides, nucleosides, drugs, nucleoproteins, lipoproteins, carbohydrates, glycoproteins, steroids, lipids, and other biologically active materials can also be prepared. This method is useful for designing a wide variety of biological mimics that are more stable than their natural counterparts, because they are typically prepared by the free radical polymerization of functional monomers, resulting in a compound with a nonbiodegradable backbone. Other methods for designing such molecules include, for example, drug design based on structure activity relationships which require the synthesis and evaluation of a number of compounds and molecular modeling.

Peptides which bind to a LCP component may also be identified by conventional screening methods such as phage display procedures (e.g., methods described in Hart, et al., *J. Biol. Chem.* 269:12468 (1994)). Hart et al. report a filamentous phage display library for identifying novel peptide ligands for mammalian cell receptors. In general, phage display libraries using, e.g., M13 or fd phage, are prepared using conventional procedures such as those described in the foregoing reference. The libraries display inserts containing from 4 to 80 amino acid residues. The inserts optionally represent a completely degenerate or a biased array of peptides. Ligands that bind are obtained by selecting those phages which express on their surface a ligand that binds to the molecule of interest. These phages then are subjected to several cycles of reselection to identify the peptide ligand-expressing phages that have the most useful binding characteristics. Typically, phages that exhibit the best binding characteristics (e.g., highest affinity) are further characterized by nucleic acid analysis to identify the particular amino acid sequences of the peptides expressed on the phage surface and the optimum length of the expressed peptide to achieve optimum binding. Alternatively, such peptide ligands can be selected from combinatorial libraries of peptides containing one or more amino acids. Such libraries can further be synthesized which contain non-peptide synthetic moieties which are less subject to enzymatic degradation compared to their naturally-occurring counterparts.

To determine whether a peptide binds to a LCP component any known binding assay may be employed. For example, the peptide may be immobilized on a surface and then contacted with a labeled LCP component. The amount of the LCP component which interacts with the peptide or the amount which does not bind to the peptide may then be quantitated to determine whether the peptide binds to the LCP component A surface, for example, having a monoclonal antibody with known specificity immobilized thereto may serve as a positive control.

Screening of binding peptides, also can be carried out utilizing a competition assay. If the peptide being tested competes with, for example, a monoclonal antibody with known specificity or some other ligand, as shown by a decrease in binding of the monoclonal antibody or ligand, then it is likely that the peptide and the monoclonal antibody or ligand bind to the same, or a closely related, epitope. Still another way to determine whether a peptide has the specificity of a monoclonal antibody or ligand with known specificity is to preincubate the monoclonal antibody (or ligand) with the LCP component with which it is normally reactive, and then add the peptide being tested to determine if the peptide being tested is inhibited in its ability to bind the LCP component. Other assays will be apparent to those of skill in the art.

As mentioned above, the binding peptide can be an antibody or fragment thereof. Antibodies are well known to those of ordinary skill in the science of immunology. As used herein, the term "antibody" means not only intact antibody molecules but also fragments of antibody molecules retaining binding ability. Such fragments are also well known in the art and are regularly employed both in vitro and in vivo. In particular, as used herein, the term "antibody" means not only intact immunoglobulin molecules but also the well-known active fragments $F(ab')_2$, and Fab. $F(ab')_2$, and Fab fragments which lack the Fc fragment of intact antibody, clear more rapidly from the circulation, and may have less non-specific tissue binding of an intact antibody (Wahl et al., *J. Nucl. Med.* 24:316-325 (1983)).

According to one embodiment, the antibody is an intact soluble monoclonal antibody. An intact soluble monoclonal antibody, as is well known in the art, is an assembly (f polypeptide chains linked by disulfide bridges. Two principle polypeptide chains, referred to as the light chain and heavy chain, make up all major structural classes (isotypes) of antibody. Both heavy chains and light chains are further divided into subregions referred to as variable regions and constant regions. As used herein the term "monoclonal antibody" refers to a homogenous population of immunoglobulins which specifically bind to an epitope (i.e. antigenic determinant).

Significantly, as is well-known in the art, only a small portion of an antibody molecule, the paratope, is involved in the binding-of the antibody to its epitope (see, in general, Clark, W. R. (1986) The Experimental Foundations of Modern Immunology. Wiley & Sons, Inc., New York; Roitt, I. (1991) Essential Immunology, 7th Ed., Blackwell Scientific Publications, Oxford). The pFc' and Fc regions of the antibody, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. An isolated $F(ab')_2$ fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', $F(ab')_2$ and Fv are used consistently with their standard immunological meanings [Klein, *Immunology* (John Wiley, New York, N.Y., 1982); Clark, W. R. (1986) *The Experimental Foundations of Modern Immunology* (Wiley & Sons, Inc., New York); Roitt, I. (1991) *Essential Immunology*, 7th Ed., (Blackwell Scientific Publications, Oxford)].

Therefore, antibodies of the invention may be single chain antibodies or may be single domain antibodies (intrabodies or intracellular antibodies). Intrabodies are generally known in the art as single chain Fv fragments with domains of the immunoglobulin heavy (VH) and light chains (VL). Well-known functionally active antibody fragments include but are not limited to F(ab')$_2$, Fab, Fv and Fd fragments of antibodies. These fragments which lack the Fc fragment of intact antibody, clear more rapidly from the circulation, and may have less non-specific tissue binding than an intact antibody (Wahl et al., *J. Nucl. Med.* 24:316-325 (1983)). For example, single-chain antibodies can be constructed in accordance with the methods described in U.S. Pat. No. 4,946,778 to Ladner et al. Such single-chain antibodies include the variable regions of the light and heavy chains joined by a flexible linker moiety. Methods for obtaining a single domain antibody ("Fd") which comprises an isolated variable heavy chain single domain, also have been reported (see, for example, Ward et al., *Nature* 341:644-646 (1989), disclosing a method of screening to identify an antibody heavy chain variable region ($V_H$ single domain antibody) with sufficient affinity for its target epitope to bind thereto in isolated form). Methods for making recombinant Fv fragments based on known antibody heavy chain and light chain variable region sequences are known in the art and have been described, e.g., Moore et al., U.S. Pat. No. 4,462,334. Other references describing the use and generation of antibody fragments include e.g., Fab fragments (Tijssen, Practice and Theory of Enzyme Immunoassays (Elsevieer, Amsterdam, 1985)), Fv fragments (Hochman et al., Biochemistry 12: 1130 (1973); Sharon et al., Biochemistry 15: 1591 (1976); Ehrilch et al., U.S. Pat. No. 4,355,023) and portions of antibody molecules (Audilore-Hargreaves, U.S. Pat. No. 4,470,925). Thus, those skilled in the art may construct antibody fragments from various portions of intact antibodies without destroying the specificity of the antibodies for their target.

As is well-known in the art, the complementarity determining regions (CDRs) of an antibody are the portions of the antibody which are largely responsible for antibody specificity. The CDRs directly interact with the epitope of the antigen. In both the heavy chain and the light chain variable regions of IgG immunoglobulins, there are four framework regions (FR1 through FR4) separated respectively by three complementarity determining regions (CDR1 through CDR3). The framework regions (FRs) maintain the tertiary structure of the paratope, which is the portion of the antibody which is involved in the interaction with the antigen. The CDRs, and in particular the CDR3 regions, and more particularly the heavy chain CDR3 contribute to antibody specificity. Because these CDR regions and in particular the CDR3 region confer antigen specificity on the antibody these regions may be incorporated into other antibodies or peptides to confer the identical specificity onto that antibody or molecule.

Antibodies to the LCP components can be produced with methods routine in the art. The following is a description of a method for developing a monoclonal antibody specific for MBL. The description is exemplary and is provided for illustrative purposes only.

Female Balb/C mice are initially inoculated (i.p.) with 250 ul of the following mixture: 250 µl Titermax mixed with 100 µg human MBL in 250 µl PBS. The following week and for three consecutive weeks the mice are injected with 50 µg hMBL in 250 PBS. On the 4th week the mice are injected with 25 µg MBL in 250 µl PBS and the mice are fused 4 days later. The fusion protocol is adapted from *Current Protocols in Immunology*. The splenocytes are fused 1:1 with myelinoma fusion partner P301 from ATCC using PEG 150 at 50% w/v. The fused cells are plated at a density of $1.25 \times 10^6$/m with 100 µl/well of a 96 well microtiter plate. The fusion media consists of Deficient DME high glucose, Pen/Strep (50,000 U pen, 50,000 µg strep per liter), 4 mM L-glutamine, 20% fetal bovine serum, 10% thyroid enriched media, 1% OPI, 1% NEAA, 1% HAT, and 50 µM 2-mercaptoethanol. The cells are fed 100 µu/well on day one and 100/well media are exchanged on days 2, 3, 4, 7, 9, 11, and 13. The last media change before primary screening consists of HAT substituted for the 1% HT. All subsequent feedings are done with fusion media minus the minus HT or HAT. Screening is done with human MBL plated to plastic FLISA plates (96 well plates). Purified hMBL is plated in each well at 50 µl volume containing 2 µg/ml MBL in 2% sodium carbonate buffer. The plates are then blocked with 3% BSA in PBS. Tissue culture media (50 µl) is placed in the wells and incubated for 1 hour at room temperature. The plates are washed and a secondary HRP labeled goat anti-mouse IgG antibody is used for detection. Colorimetric analysis is done with ABTS and read at 405 nm. Positive controls consists of a polyclonal antibody to human MBL. Cells are then grown in media consisting of the following: DMEM high glucose no-I-glut, sod, pyruvate 500 ml (Irvine Scientific #9024), heat inactivated Hyclone 10%, 1% Non-essential amino acids, 4 mM L-glutamine, 100 U/ml penicillin and 100 µg/ml streptomycin. All positive wells are then screened for function in a secondary screen.

The antibodies may be human antibodies (e.g., a human monoclonal antibody) or intact humanized monoclonal antibodies. A "humanized monoclonal antibody" as used herein is a monoclonal antibody or functionally active fragment thereof having human constant regions and an antigen-binding region (e.g., CDR3) from a mammal of a species other than a human. Humanized monoclonal antibodies may be made by any method known in the art. Humanized monoclonal antibodies, for example, may be constructed by replacing the non-CDR regions of a non-human mammalian antibody with similar regions of human antibodies while retaining the epitopic specificity of the original antibody. For example, non-human CDRs and optionally some of the framework regions may be covalently joined to human FR and/or Fc/pFc' regions to produce a functional antibody. There are entities in the United States which will synthesize humanized antibodies from specific murine antibody regions commercially, such as Protein Design Labs (Mountain View Calif.). For instance, a humanized form of a murine anti-MBL antibody could be prepared and used according to the methods of the invention.

European Patent Application 0239400, the entire contents of which is hereby incorporated by reference, provides an exemplary teaching of the production and use of humanized monoclonal antibodies in which at least the CDR portion of a murine (or other non-human mammal) antibody is included in the humanized antibody. Briefly, the following methods are useful, as examples for constructing a humanized monoclonal antibody including at least a portion of a mouse CDR. A first replicable expression vector including a suitable promoter operably linked to a DNA sequence encoding a variable domain of an immunoglobulin (Ig) heavy or light chain and the variable domain comprising framework regions from an human antibody and a CDR region of a murine antibody is prepared. Optionally a second replicable expression vector is prepared which includes a suitable promoter operably linked to a DNA sequence encoding at least the variable domain of a complementary human Ig light or heavy chain respectively. A cell line is then transformed with the vector(s). Preferably the cell line is an immortalized mammalian cell line of lymphoid origin, such as a myeloma, hybridoma, trioma, or quadroma cell line, or is a normal lymphoid cell which has been immortalized by transformation with a virus. The transformed cell line is then cultured under conditions known to those of skill in the art to produce the humanized antibody.

As set forth in European Patent Application 0239400 several techniques are well known in the art for creating the particular antibody domains to be inserted into the replicable vector. (Vectors and recombinant techniques are discussed in greater detail below.) For example, the DNA sequence encoding the domain may be prepared by oligonucleotide synthesis. Alternatively a synthetic gene lacking the CDR regions in which four framework regions are fused together with suitable restriction sites at the junctions, such that double stranded synthetic or restricted subcloned CDR cassettes with sticky ends could be ligated at the junctions of the framework regions. Another method involves the preparation of the DNA sequence encoding the variable CDR containing domain by oligonucleotide site-directed mutagenesis. Each of these methods is well known in the art. Therefore, those skilled in the art may construct humanized antibodies containing a murine CDR region without destroying the specificity of the antibody for its epitope.

Human monoclonal antibodies may be made by any of the methods known in the art, such as those disclosed in U.S. Pat. No. 5,567,610, issued to Borrebaeck et al., U.S. Pat. No. 5,565,354, issued to Ostberg, U.S. Pat. No. 5,571,893, issued to Baker et al, Kozber, J. Immunol. 133: 3001 (1984), Brodeur, et al., Monoclonal Antibody Production Techniques and Applications, p. 51-63 (Marcel Dekker, Inc, new York, 1987), and Boerner et al., J. Immunol., 147: 86-95 (1991). In addition to the conventional methods for preparing human monoclonal antibodies, such antibodies may also be prepared by immunizing transgenic animals that are capable of producing human antibodies (e.g., Jakobovits et al., PNAS USA, 90: 2551 (1993), Jakobovits et al., Nature, 362: 255-258 (1993), Bruggermann et al., Year in Immuno., 7:33 (1993) and U.S. Pat. No. 5,569,825 issued to Lonberg).

Alternatively, monoclonal antibodies to the various LCP components known in the art may be used in the assays provided herein. For example, known antibodies that bind MBL include monoclonal antibodies produced by the hybridomas deposited with the ATCC under ATCC Accession No. (HB-12621), ATCC Accession No. (HB-12620) and ATCC Accession No. (HB-12619); anti-C4 antibodies can be obtained from Cappel/ICN Pharmaceuticals (Aurora, Ohio), and anti-C3 antibody (mouse anti-human C3 clone 7C12) is known in the art (Tosic et al., 1989).

The agents that specifically bind to the LCP component(s) can be detectably labeled. Detectable labels include near-infrared fluorochromes, radiolabels, fluorescent labels, chromophores, enzyme labels, free radical labels, avidin-biotin labels or bacteriophage labels. Conjugation of the agent and label can be accomplished using techniques known to the art, such as methods of protein conjugation or dye labeling as performed by Rockland Immunochemicals (Gilbertsville, Pa.) and the methods of Chard, *Laboratory Techniques in Biology*, "An Introduction to Radioimmunoassay and Related Techniques," North Holland Publishing Company (1978).

Near-infrared fluorochromes include IRDye® 800CW, IRDye® 700DX and AlexaFluor 680.

Typical fluorescent labels include fluorescein isothiocyanate, rhodamine, phycoerythrin, phycocyanin, allophycocyanin, and fluorescamine.

Typical chemiluminescent compounds include luminol, isoluminol, aromatic acridinium esters, imidazoles, and the oxalate esters.

Typical bioluminescent compounds include luciferin, and luciferase. Typical enzymes include alkaline phosphatase, β-galactosidase, glucose-6-phosphate dehydrogenase, maleate dehydrogenase, glucose oxidase, and peroxidase.

The labels when more than one LCP component is measured in an assay can be the same or they can be different. For example, labels that can be detected at different wavelengths can be used. When different labels are used, in some embodiments, the labels can be individually detected and quantitated. Alternatively, the different labels can be detected at different points in time when the other label is no longer present. As provided above, near-infrared fluorochromes can be used and include those that can be detected at 700 nm and those that can be detected at 800 nm.

"Biological samples", as used herein, are any samples from a subject in which the assessment of LCP activation can be made. Such samples include, for example, serum, plasma and cerebrospinal fluid samples. In some embodiments, where plasma samples are analyzed; the methods can include a step whereby the plasma sample is converted to a serum sample. Methods for doing so can, in some embodiments, include using a VBS$^{++}$ buffer supplemented with calcium chloride (such as with a 1:1 dilution of sample to buffer). The methods can further include removing the fibrin clots that result.

The samples can be obtained, in some embodiments, from subjects that have or are suspected of having a LCP-mediated disease. Such subjects are readily identifiable by those of ordinary skill in the art. A "LCP-mediated disease" as used herein is any condition, disease or disorder which involves in its onset or pathogenesis of LCP complement activation. Therefore, included are those that involve cellular injury caused by LCP complement activation. LCP-mediated diseases include, for example, acute respiratory distress syndrome, arteriosclerosis, arthritis (such as rheumatoid arthritis), atherosclerosis, cancer (such as breast cancer, colorectal cancer, esophageal squamous cell carcinoma, lung cancer and prostate-cancer), cardiopulmonary bypass, cardiovascular disease, chronic angioedema, coronary artery disease, diabetes, dialysis, infection (such as respiratory infection, *P. aeruginosa* infection, sepsis (such as in burn patients)), ischemia and reperfusion (such as that involved in ischemic heart disease and gastrointestinal ischemia and reperfusion), autoimmune disease, lupus (such as SLE), meningococcal disease, myocardial infarction, *Neisseria* menningitis, nephritis (such as IGA nephritis and membranoproliferative glomerulonephritis), neurological disease, neuropathic pain, stroke, thoracoabdominal aortic aneurysm repair and transplantation. Each of these is well-known in the art and/or described, for instance, in *Harrison's Principles of Internal Medicine* (McGraw Hill, Inc., New York).

The methods provided herein can be used to assess LCP activation in a subject having or suspected of having a LCP-mediated disease. Such methods can also include the step of selecting a treatment for the subject based on the LCP activation assessment. The treatment selected can be based on the particular type of LCP-mediated disease the subject has and/or the results from the assays provided herein.

The methods provided can also be used to compare samples from subjects that have or are suspected of having a LCP-mediated disease with samples from subjects that are disease free or from the general population.

The methods provided can also be used to examine samples from subjects that have suffered from a myocardial infarction or have undergone cardiovascular surgery.

Kits are also provided that can be used for performing the methods of the invention provided herein. In one embodiment, therefore, a kit is provided that includes an agent that specifically binds MBL and an agent that specifically binds at least one other LCP component. The kit, therefore, can include an agent that specifically binds MBL and an agent that specifically binds MASP-2. In another embodiment, the kit can include an agent that specifically binds MBL and an agent that specifically binds C3 or C4. In still another embodiment, the kit includes an agent that specifically binds MBL, an agent that specifically binds MASP-2, an agent that specifically binds C3 and an agent that specifically binds C4. In yet another embodiment, the kit includes an agent that specifically binds MBL, an agent that specifically binds C3 and an agent that specifically binds-C4.

In another embodiment, a kit is provided that includes an agent that specifically binds ficolin and an agent that specifically binds at least one other LCP component. The kit, therefore, can include an agent that specifically binds ficolin and an agent that specifically binds MASP-2. In another embodiment, the kit can include an agent that specifically binds ficolin and an agent that specifically binds C3 or C4. In still another embodiment, the kit includes an agent that specifically binds ficolin, an agent that specifically binds MASP-2, an agent that specifically binds C3 and an agent that specifically binds C4. In yet another embodiment, the kit includes an agent that specifically binds ficolin, an agent that specifically binds C3 and an agent that specifically binds C4.

In still another embodiment, a kit is provided that includes an agent that specifically binds C4.

The kits provided can also include a buffer comprising a calcium chelator. The buffer, in some embodiments, can also include a competitive inhibitor, such as a competitive inhibitor of MBL. Such inhibitors are described elsewhere herein.

The kits provided can also include instructions for assessing LCP activation and/or MASP-2 function.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

Measurement of MBL, MASP-2, C4 and C3

Materials and Methods
Plate Preparation.

384-well clear flat bottom HB microplates (Corning Incorporated, Corning, N.Y.) were coated with 25 µl per well of 0.5 mg/ml mannan (Sigma, St. Louis, Mo.) in sodium carbonate/bicarbonate buffer, pH 9.8. Plates were incubated overnight at 40° C. The following day, plates were blocked with 110 µl per well of 3% BSA in PBS without calcium or magnesium (Sigma) for two hours at room temperature. Plates were then washed three times with PBS/Tween 20 (0.5%), once with PBS, and once with veronal buffered saline (VBS). Excess volume was removed, and plates were stored at −30° C.

IRDye-Labeled Antibodies

All antibodies were labeled using long-wavelength near-infrared fluorochromes (Rockland Immunochemicals, Gilbertsville, Pa.) IRDye800 or IRDye700. Fluorochrome to protein quality control was performed by Rockland Immunochemicals, and optimal dilutions for ELISA analysis were defined. Antibodies used for conjugation were as follows: IRDye800 labeled 2A9 (mouse anti-recombinant human MBL), IRDye800 goat anti-human C4 (ICN Pharmaceuticals, Aurora, Ohio), IRDye700 mouse anti-recombinant human MASP-2 and IRDye700 goat anti-human C3 (ICN Pharmaceuticals).

MBL-Dependent LCP ELISA

All ELISA analyses were performed using the Odyssey Infrared Imaging system (LICOR Biosciences, Lincoln, Nebr.), and all sample processing for plates utilized a fully automated liquid handling and plate washing system. Prepared 384-well mannan plates were thawed at room temperature (25° C.) for 15 minutes. Pooled human serum (Fisher-MP Biomedicals, Pittsburgh, Pa.) was then added to plates at 15 µl per well and serially diluted using the Precision 96/384 well Microplate Pipetting System (BIO-TEK Instruments Inc., Winooski, Vt.). Sample diluent was hypertonic buffer (20 mM Tris, 1M NaCl, 10 mM $CaCl_2$, 0.05% Triton X, 1% BSA), and hypertonic buffer alone was added to mannan wells as a background control. Plates were then incubated at 37° C. for 30 minutes and then washed (Buffer A: 145 mM NaCl, 10 mM HEPES, 10 mM $CaCl_2$, 490 mM $MgCl_2$, 0.05% Tween) four times using the EIx405 Microplate Washer with Bio-Stack Microplate Stacker (BIO-TEK). MBL and MASP-2 were detected by addition of 15 µl per well of 1:1000 IRDye800 2A9 (anti-MBL) and 1:500 IRDye700 anti-MASP-2 diluted in Wash 10+0.05% Tween, incubated for one hour at 25° C., washed (×3 with Buffer A) and then read on the Odyssey Infrared Imaging system (LICOR) concurrently at 700 nm and 800 nm. Following this first reading, plates were washed three times with Buffer B: (50 mM Tris-HCl, 150 mM NaCl, 10 mM EDTA, 0.05% Tween-20, 100 mM mannose at pH 7.8). Plates were read again on the Odyssey Infrared Imaging system (LICOR)-concurrently at 700 nm and 800 nm to establish baseline fluorescence following removal of the primary antibody cocktail mix. Next, the second antibody cocktail to determine C3 and C4 deposition was performed by addition of 15 µl per well of 1:1000 IRDye700 anti-C3 and IRDye800 anti-C4 (diluted in Buffer A), incubated for one hr at 25° C., washed (4× with Buffer A) and read on the Odyssey Infrared Imaging system (LICOR), concurrently at 700 nm and 800 nm. Analytical accuracy of MBL, MASP-2, C4 and C3 is represented by the average integrated intensities of pooled human serum standards (Fisher-MP Biomedicals) in triplicate per plate, and in triplicate per assay (intra and inter CV values expressed as a percentage). Pooled human serum was assigned a lot number, and frozen in aliquots at −80° C.

Results

Figure 2:
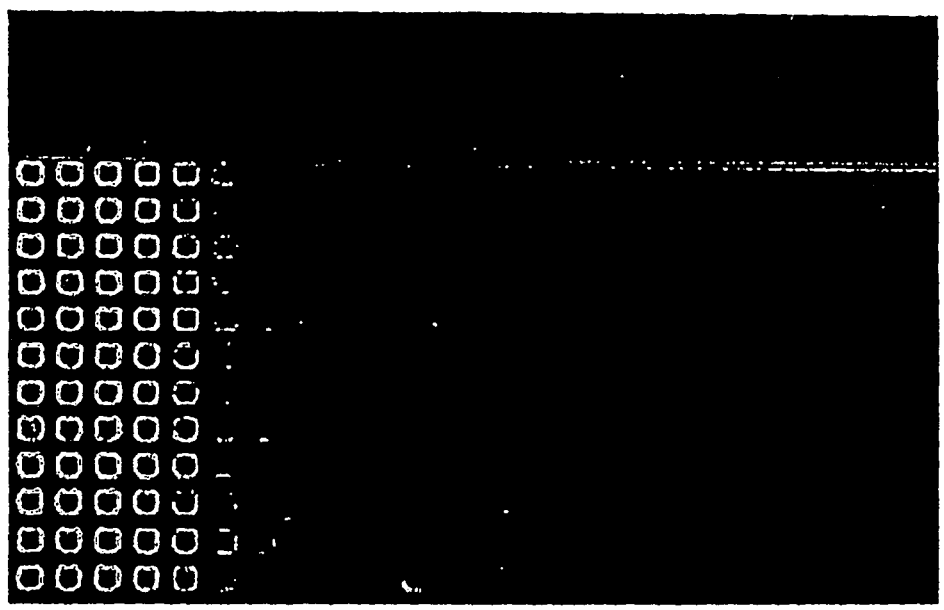
FIG. 2 demonstrates the deposition of MBL indicated by binding of the IRDye800-labeled anti-MBL mAb (2A9) and visualized on the 800 nm infra-red channel.
Figure 3A:
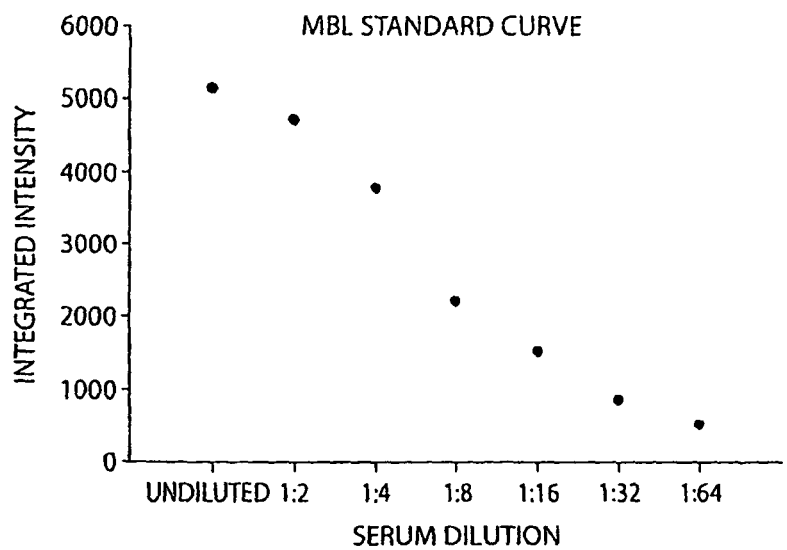
FIG. 3 provides results for MBL and MASP-2 deposition. Triplicate values of each serum undiluted sample and dilutions were averaged and expressed as units of Integrated Intensity for MBL (FIG. 3A). MASP-2 in pooled human serum/plasma were screened for using the second infra-red channel available for analysis (700 nm) (FIG. 3B).

Important steps of the LCP are outlined in FIG. 1, which includes the four endpoints of this ELISA: MBL, MASP-2, C4 and C3. Mannan is one of the major oligosaccharide ligands for MBL, and recognition of mannan is indicative of functional MBL activity. Therefore, MBL deposition on mannan-coated substrates is an indicator of functional MBL levels in patient serum/plasma. Deposition of MBL was indicated by binding of the IRDye800-labeled anti-MBL mAb (2A9) and visualized on the 800 nm infra-red channel; a representative example of which can be observed in FIG. 2. Triplicate values of each serum undiluted sample and dilutions were averaged and expressed as units of Integrated Intensity (FIG. 3a).

Figure 3B:
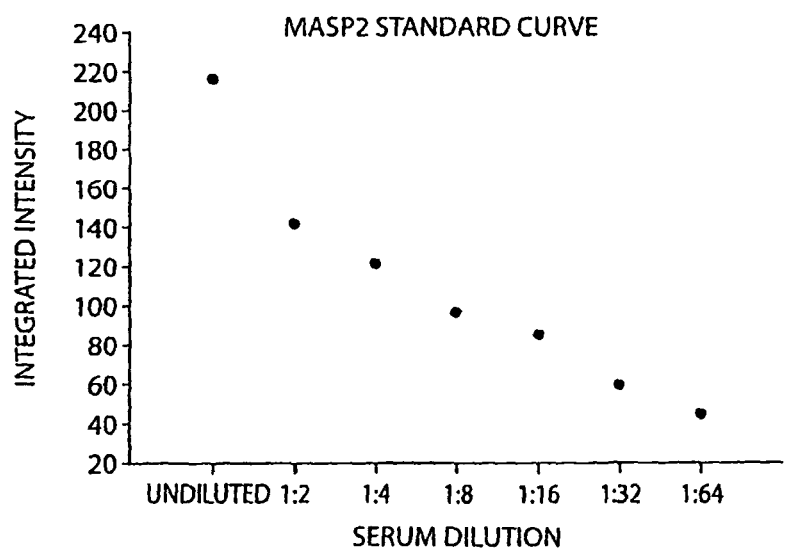

The mannose binding lectin associated serine protease 2 (MASP-2) is a regulator in the activation of the LCP via its recognition of MBL. MASP-2 activation is required for enzymatic cleavage of C4 and C2 to form the C3 convertase C4b2a, which results in C3 cleavage and deposition. The dual channel technology of the LCP assay was used to analyze levels of MASP-2 present in patient serum/plasma. As observed in FIG. 3b, this enzymatic protease in pooled human serum/plasma can be screened for using the second infra-red channel available for analysis (700 nm).

The next step of this assay regenerates the LCP analysis-platform by removing non-covalently bound MBL and MASP-2 (and their associated antibodies). The regeneration buffer removes the $Ca^{2+}$ required for the interaction of MBL, MASP-2 and target ligand, while additionally containing a competitive MBL ligand, mannose. Following regeneration, fluorescence on both the 700 and 800 nm channels were returned to background levels (FIG. 3). Because components of LCP activation downstream of MBL and MASP-2 (i.e., C3 and C4) are deposited and covalently associated with the target (mannan plate), regeneration of the analysis platform increases the analysis from a two end-point assay to a four-endpoint analysis of LCP activation.

Figure 4A:
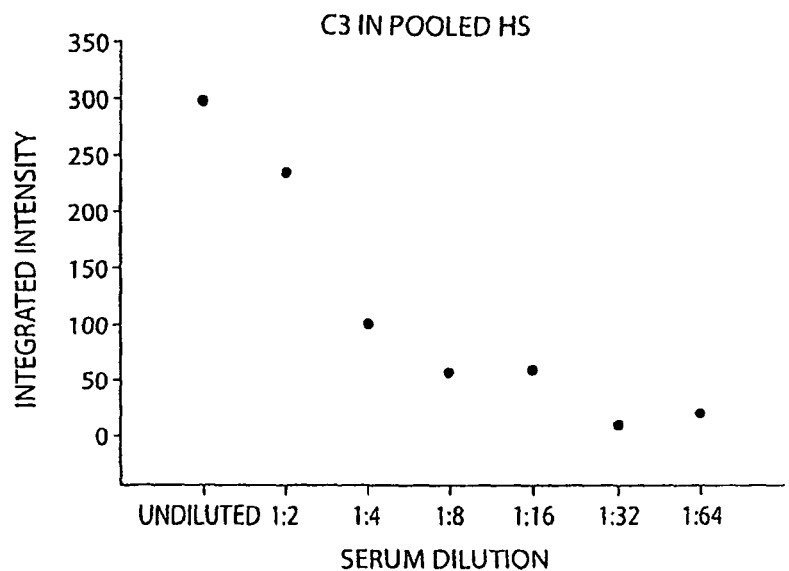
FIG. 4A shows that C4 is deposited, as detected by IRDye800-labeled anti-C4. Deposition of C3 on mannan plates was detected by IRDye700-labeled anti-C3 (FIG. 4B).

As indicated in FIG. 1, C4 is an important indicator of MBL ligand-recognition and of functional MASP-2 concentrations. Following the regeneration step, C4 cleavage and deposition on mannan plates incubated with human serum was investigated. The same wells demonstrated successful binding of MBL and MASP-2 on mannan prior to the regeneration step, and background levels of fluorescence after the regeneration step. As seen in FIG. 4a, C4 is deposited on the plate, as detected by IRDye800-labeled anti-C4.

Figure 4B:
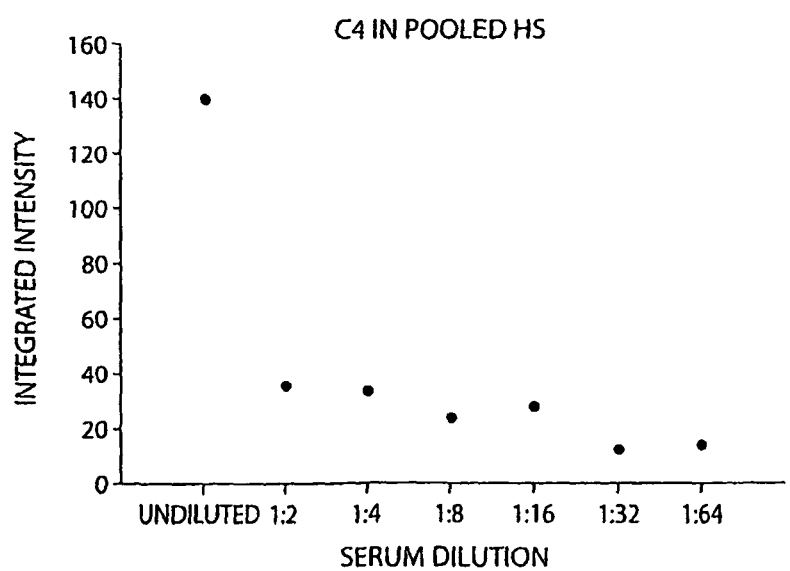
FIG. 4 illustrates the deposition of C4 and C3.

Additionally, using the 700 nm channel activation of the LCP at the level of C3 convertases can be assessed. Deposition of C3 on the plate signifies formation of a functional C3 convertase and thus, C2's presence indirectly. Deposition of C3 on mannan plates was detected by IRDye700-labeled anti-C3 (FIG. 4b).

References for Example 1
1. Collard, C. D., M. C. Montalto, W. R. Reenstra, J. A. Buras, and G. L. Stahl. 2001. Endothelial oxidative stress activates the lectin complement pathway: role of cytokeratin 1g . Am. J. Pathol. 159:1045-1054.
2. Montalto, M. C., C. D. Collard, J. A. Buras, W. R. Reenstra, R. McClaine, D. R. Gies, R. P. Rother, and G. L. Stahl. 2001. A keratin peptide inhibits mannose-binding lectin. J. Immunol. 166:4148-4153.
3. Jordan, J. E., M. C. Montalto, and G. L. Stahl. 2001. Inhibition of mannose-binding lectin reduces postischemic myocardial reperfusion injury. Circ 104:1413-1418.
4. Walsh, M. C., T. Bourcier, K. Takahashi, L. Shi, M. N. Busche, R. P. Rother, S. D. Solomon, R. A. B. Ezekowitz, and G. L. Stahl. 2005. Mannose Binding Lectin is a Regulator of Inflammation That Accompanies Myocardial Ischemia and Reperfusion Injury. J. Immunol. 175.
5. Windsor, A. C. J., C. J. Walsh, P. G. Mullen, D. J. Cook, B. J. Fisher, C. R Blocher, S. K. Leeper-Woodford, H. J. Sugerman, and A. A. Fowler, III. 1993. Tumor necrosis factor-a blockade prevents neutrophil CD18 receptor upregulation and attenuates acute lung injury in porcine sepsis without inhibition of neutrophil oxygen radical generation. J. Clln Invest. 91:1.459-1468.
6. Hart, M. L., K. A. Ceonzo, L. A. Shaffer, K. Takahashi, L. Shi, W. R. Keenstra, J. A. Buras, R. A. B. Ezekowitz, and Q. L. Stahl. 2005. Gastrointestinal ischemia-reperfusion injury is lectin complement pathway dependent without involving C1q.
7. Saevarsdottir, S., O. O. Oskarsson, T. Aspelund, G. Eiriksdottir, T. Vikingsdottir, V. Gudnason, and H. Valdimarsson. 2005. Mannan binding lectin as an adjunct to risk assessment for myocardial infarction in individuals with enhanced risk. J. Exp. Med. 201: 117-125.
8. Fiane, A. E., V. Videm, P. S. Lingaas, L. Heggelund, E. W. Nielsen, O. R. Geiran, M. Fung, and T. E. Mollnes. 2003. Mechanism of complement activation and its role in the inflammatory response after thoracoabdominal aortic aneurysm repair. Circ 108:849-856.
9. DeVries, B., S. J. Walter, C. J. Peutz-Kootstra, T. G. Wolfs, L. W. van Heurn, and W. A. Buurman. 2004. The mannose-binding lectin-pathway is involved in complement activation in the course of renal ischemia—reperfusion injury. Am. J. Pathol. 165:1677-1688.
10. Garred, P., H. O. Madsen, P. Halberg, J. Petersen, G. Kronborg, A. Svejgaard, V. Andersen, and S. Jacobsen. 1999. Mannose-binding lectin polymorphisms and susceptibility to infection in systemic lupus erythematosus. Arthritis Rheum. 42:1945-2152.
11. Graudal, N. A., C. Homann, H. Q. Madsen, A. Svejgaard, A. G. Jurik, H. K. Graudal, and P. Garred. 1998. Mannan-binding lectin in rheumatoid arthritis. A longitudinal study. J. Rheumatol/. 25:629-635.
12. Endo, M., H. Ohi, L Ohsawa, T. Fujita, M. Matsushita, and T. Fujita. 1998. Glomerular deposition of mannose-binding lectin (MBL) indicates a novel mechanism of complement activation in IgA nephropathy. Nephrol. Dial. Transplant. 13:1984-1990.
13. Ytting, H., I. J. Christensen, S. Thiel, J. C. Jensenius, and H. J. Nielsen. 2005. Serum mannan-binding lectin-associated serine protease 2 levels in colorectal cancer: relation to recurrence and mortality. Clin. Cancer Res. 11:1441-1446.
14. Moller-Kristensen, M., J. C. Jensenius, L. Jensen, N. Thielens, V. Rossi, G. Arlaud, and S. Thiel, 2003. Levels of mannan-binding lectin-associated serine protease-2 in healthy individuals. J. Immunol. Methods 282:159-167.

Example 2

Measurement of MBL, C4 and C3

Materials and Methods

Patient Samples and Standard Serum Components

Serum samples were collected from informed consent donors, following IRB approval, from the Brigham and Women's Hospital population, Boston, Mass. Individual serum samples were pooled to create a standardized human sera stock (PLS) for assay evaluation and validation. Each PLS batch was assigned a lot number, and frozen in aliquots at −80° C. for future FLISA use. Serum samples representing various homozygotic MBL haplotypes were from informed consent donors from the Brigham and Women's Hospital, and the Texas Heart Institute, Baylor College of Medicine, Houston, Tex.

The MBL content of the PLS was standardized using MBL-deficient serum and a quality controlled purified MBL protein standard (Staten Serum Institut, Copenhagen, Denmark). Purified complement components C4b and C3b (Complement Technologies Inc., San Diego, Calif.) were used as quality control samples and to standardize the downstream activated components of the MBL-dependent LCP in the PLS.

Antibodies

All labeled antibodies utilized long-wavelength near-infrared fluorochromes IRDye® 800CW or IRDye® 700DX (Rockland Immunochemicals, Gilbertsville, Pa.) or AlexaFluor 680 (Molecular Probes/Invitrogen, Carlsbad, Calif.). Fluorochrome to protein conjugation was performed by Rockland Immunochemicals, or according to manufacturer's instructions for dye labeling. Optimal dilutions for FLISA labeled antibodies were defined by our laboratory in pilot studies. Antibodies used for conjugation are as follows: IRDye8.00 labeled 2A9 (mouse anti-human MBL (Collard et al., 2000), goat anti-human C4 (Cappel/ICN Pharmaceuticals, Aurora, Ohio); AlexaFluor 680 mouse anti-human C3 clone 7C12 (Tosic et al., 1989), and donkey anti-goat IgG IRDye800 (Cappel/ICN)). Optimal concentrations of each antibody were determined in pilot studies.

Plate Preparation

High binding, 384-well, clear, flat bottom microplates (Corning Incorporated, Corning, N.Y.) were coated with 25 µl per well of 0.5 mg/ml mannan (Sigma, St. Louis, Mo.) in sodium carbonate/bicarbonate buffer pH 9.8. Plates were incubated overnight at 4° C. The plates were then blocked with 110 µl per well of 3% BSA in PBS without calcium or magnesium (Sigma) for two hours at room temperature. Plates were then washed three times with PBS/Tween 20 (0.5%), once with PBS, and once with veronal buffered saline (VBS). Excess volume was removed from the plates, which were covered and stored at −30° C.

MBL-Dependent LCP FLISA

All FLISA analyses were performed using the Odyssey and/or Aerius Infrared Imaging systems (LICOR), and all sample processing for plates utilized a fully automated liquid handling and plate washing system (BIO-TEK Instruments Inc., Winooski, Vt.). Prepared 384-well mannan plates (protocol above) were thawed at room temperature (25° C.) for 15 minutes. Diluted plasma (see preparation below) and/or serum were then added to plates at 15 µl per well and serial diluted using the Precision 96/384 well Microplate Pipetting System (BIO-TEK Instruments Inc.). Sample diluent for serum or plasma samples was fortified veronal buffered saline (VBS$^{++}$; 143 mM NaCl, 5 mM Barbital Sodium Salt, 5 mM MgCl$_2$, 5 mM CaCl$_2$). Buffers alone were added to mannan wells as a background control. Plates were incubated at 37° C. for 30 minutes and then washed with Buffer A: (145 mM NaCl, 10 mM HEPES, 10 mM CaCl$_2$, 490 µM MgCl$_2$, 0.05% Tween) four times (Elx405 Microplate Washer with Bio-Stack Microplate Stacker; BIO-TEK Instruments Inc.). MBL was detected by addition of 15 µl per well of 1:500 IRDye800 2A9 (anti-MBL) diluted in Buffer A incubated for one hour at 25° C., washed (3× with Buffer A) and then read on the Odyssey/Aerius Infrared Imaging system (LICOR) at 800 nm. Following this first reading, plates were soaked for 15 minutes with 100 µl/well of Buffer B: (50 mM Tris-HCl, 150 mM NaCl, 10 mM EDTA, 0.05% Tween-20, 100 mM D(+)-mannose at pH 7.8), followed by 1× wash with Buffer B. Plates were read again on the Aerius/Odyssey Infrared Imaging system (LICOR) at 800 nm to establish baseline fluorochrome emittance following removal of MBL, and the primary antibody against MBL. Next, 15 µl per well of goat anti-human C4 at 1:500 (diluted in Buffer A) was added to plates and incubated for one hour at 25° C. Following a 4× wash with Buffer A; 15 µl per well of 1:1000 IRDye800 donkey anti-goat IgG, and 1:3000 AlexaFluor 680 7C12 (diluted in Buffer A; anti-C3b) were incubated for one hour at 25° C., washed (4× with Buffer A) and read on the Aerius/Odyssey Infrared Imaging system (LICOR) concurrently at 100 nm and 800 nm. Measurement of MBL (ng/ml) was interpolated from the serum or plasma dilution series, and MBL-dependent activation products (pg) were evaluated at 3% serum unless otherwise stated.

For inhibition studies, mAb 3F8 specific for human MBL (Collard et al., 2000) and anti-human factor D antibody (Stahl et al., 2003) at the concentrations indicated were added to serum at 25° C. for 30 minutes prior to plate incubation.

Plasma Preparation

Sera and citrated (3.2%) plasma samples were obtained from the same three donors. Citrated plasma (100 µl) was mixed 1:1 with VBS++ buffer supplemented to 16.3 mM calcium chloride to induce coagulation as described (Clinical Chemistry 48: 255-260, 2002;). Sera and coagulated plasma samples were allowed to clot overnight at 4° C. Sera were separated from fibrin clots by centrifugation and then used in the FLISA.

Freeze-Thaw Effects

Sera samples were aliquoted and subjected to multiple rounds of freezing (−80° C.) and thawing to room temperature. Freeze/thaw samples were then subjected to FLISA analysis.

Statistics

Samples were averaged in triplicate and expressed as mean+/− the standard error (SE). PLS integrated intensities were averaged in triplicate per plate and in quadruplicate per assay with intra- and inter-CV values expressed as a percentage. A power analysis was performed to select the appropriate sample of representative haplotypes to achieve statistical significance for functional MBL evaluation. Significance was defined as $p<0.05$.

Results

Figure 6A:
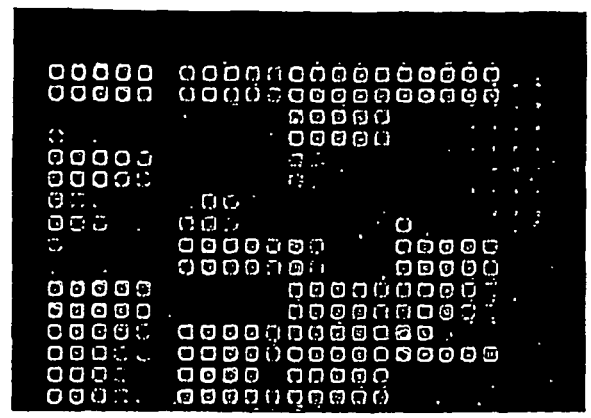
FIG. 6 provide results from an MBL-dependent LCP assay using LICOR technology. Multiple endpoints of LCP activation are concurrently analyzed on the far-infrared channels 700 nm and 800 nm. MBL (FIG. 6A) was analyzed first at 800 nm over a series of serum dilutions. Following a regeneration step (FIG. 6B) which removes non-covalently associated MBL and MASPs, covalently bound C4b and C3b were then analyzed in the same well (FIG. 6C). The left inset (FIG. 6C) represents MBL-dependent C4b analysis (green—800 nm) and MBL-dependent C3b analysis (red—700 nm), respectively. The right upper and lower insets (FIG. 6C) represent C4b and C3b deposition, respectively.
Figure 7A:
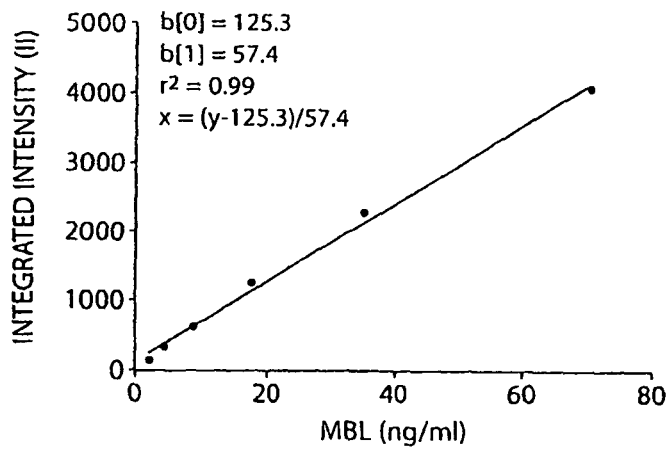
FIG. 7 illustrates quantitation of MBL in the standard PLS. A pooled human serum standard (PLS) was standardized by using MBL-deficient serum reconstituted with a human MBL standard (Staten Serum Institut, Copenhagen, Denmark). Correlation between detected units of integrated intensity (II) at 800 nm and ligand binding was performed using a linear regression model to establish MBL-dependent binding in ng/ml (FIG. 7A). Specificity of functional MBL binding was demonstrated by blocking with mAb 3F8 (FIG. 7B). Using the PLS to establish functional MBL levels (FIG. 7C), triplicate values of each donor (DN 1=donor 1, DN 2=donor 2, DN 3=donor 3, DN 4=donor 4) serum sample diluted in binding buffer are expressed as mean+/−SE.
Figure 7B:
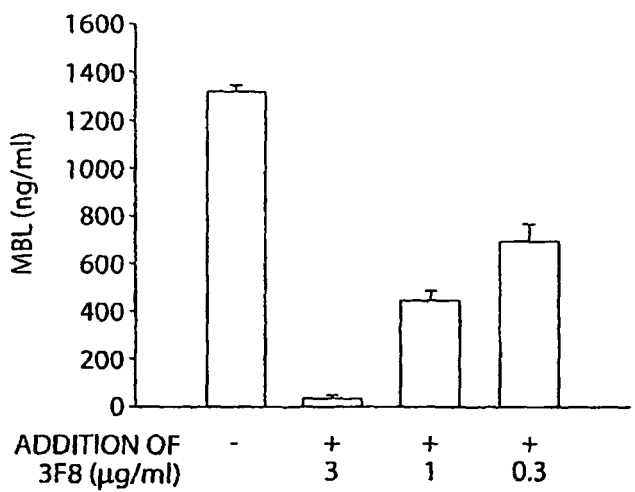
Figure 7C:
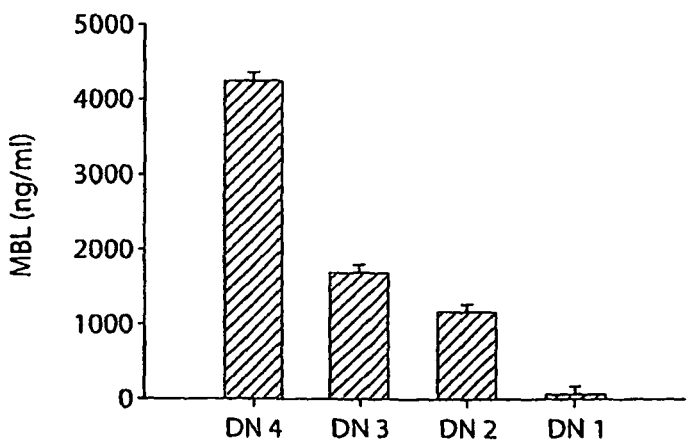

The LCP, including the MBL-dependent LCP is outlined in FIG. 5. As mannan is a major ligand for MBL, evaluation of MBL binding on mannan-coated plates can demonstrate functional MBL levels in a sera or plasma sample. MBL-binding was detected using a directly labeled IRDye800 anti-MBL mAb (2A9) visualized on the 800 nm infra-red channel observed in FIG. 6A. A pooled human serum standard (PLS) was standardized by using MBL-deficient serum (Staten Serum Institut; MBL B/B also recognized as O/O) reconstituted with a known purified human MBL-standard (Staten Serum Institut). Intra-assay coefficient variation was 4%. Correlation between detected units of integrated intensity (II) at 800 nm and ligand binding was performed using a linear regression model to establish MBL-dependent binding in ng/ml (FIG. 7A). Specificity of functional MBL binding was demonstrated by blocking with mAb 3F8 (FIG. 7B) or D-mannose. Using the PLS to establish functional MBL levels, triplicate values of individual donor serum sample diluted in binding buffer were averaged and expressed as ng/ml (FIG. 7C, DN 1-4).

Figure 6B:
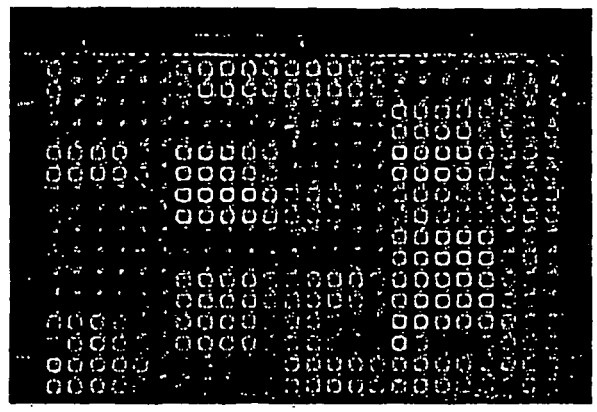

Following analysis of the functional MBL concentrations present, the plate was then regenerated by removing non-covalently bound MBL/MASP-2 complexes (and their associated detector antibodies). The regeneration buffer removes the Ca$^{2+}$ required for MBL complex binding and competitively inhibits MBL binding by addition of D-mannose to the regeneration buffer. Following regeneration, infrared emittance on the 800 nm channel was returned to background levels (FIG. 6B). Because activated components of LCP activation downstream of MBL/MASP-2 (i.e., C3b and C4b) are deposited and covalently bound, regeneration of the analysis platform increases the analysis from a single end-point assay to a 3-endpoint analysis of MBL-dependent LCP activation from one sera sample.

Figure 6C:
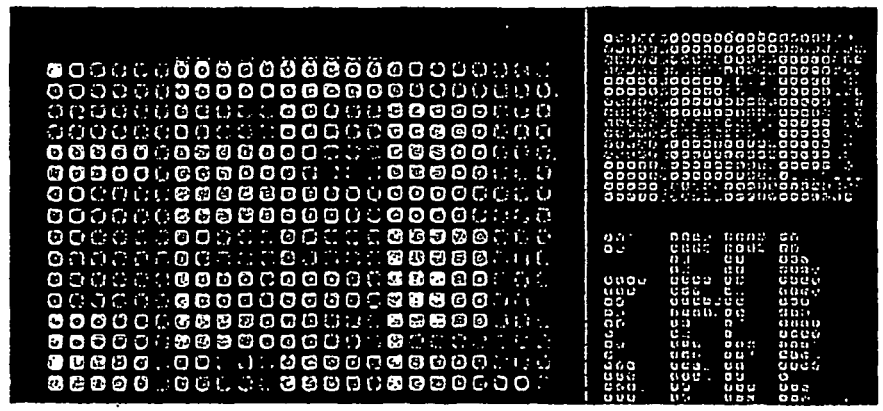

Enzymatic cleavage of C4, with consequent C4b deposition onto the mannan plate demonstrates functional MASP-2 activity (FIG. 5). Following the regeneration step, MBL/MASP-2 complex dependent C4b and C3b deposition on mannan plates from human serum were analyzed at 800 nm and 700 nm, respectively, after incubation with the detection antibodies described in Materials and Methods. As shown in FIG. 6C (left side panel), C4b and C3b were simultaneously recorded from each well. Individual scans for C4b (green) and C3b (red) are shown in the upper and lower right panels of FIG. 6C, respectively.

Figure 8A:
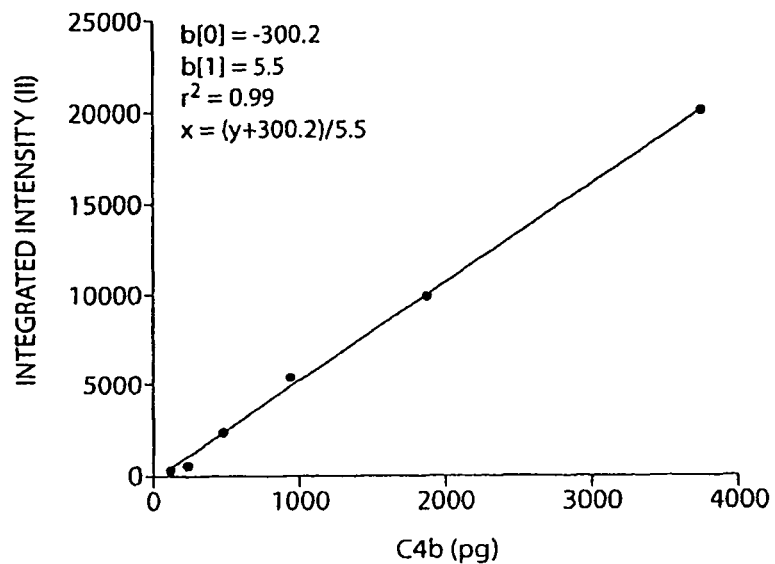
FIG. 8 demonstrates quantitation of MBL-dependent C4b deposition. A linear correlation between detected units of integrated intensity (II) at 800 nm using known amounts of C4b plated onto 384 well plates was established (FIG. 8A). The amount of MBL-dependent C4b that was bound to the mannan-coated plates following incubation of the PLS was revealed as a log-linear relationship between the integrated intensity of activated PLS deposited C4b and known amounts of C4b (FIG. 8B). Specificity for MBL-dependent C4b deposition was verified by inhibition with mAb 3F8 (FIG. 8C). Using the PLS to establish MBL-dependent C4b levels, triplicate values of each donor (DN 1=donor 1, DN 2=donor 2, DN 3=donor 3, DN 4=donor 4) serum sample diluted in binding buffer are expressed as mean+/−SE of the PLS for C4b (horizontal bars) and MBL (vertical bars).
FIGS. 8D and 9D represent the same donors at 3% sera and demonstrated MBL-dependent C4b and C3b deposition, respectively.
Figure 8B:
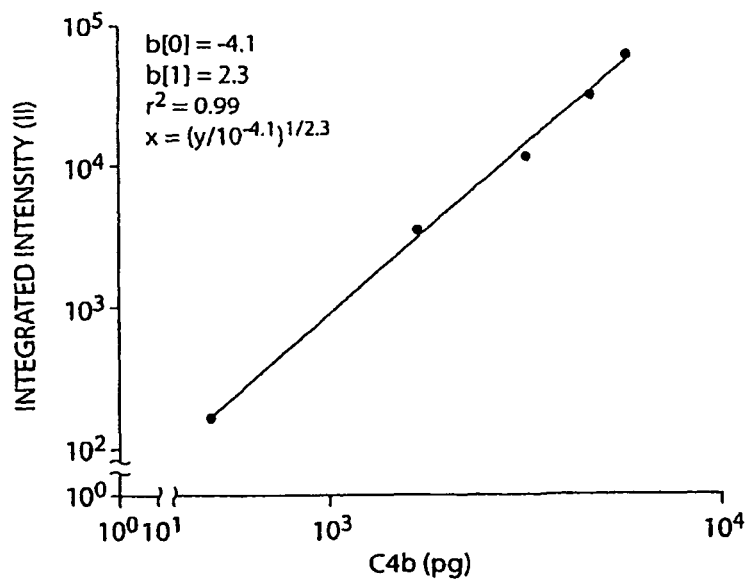
Figure 8C:
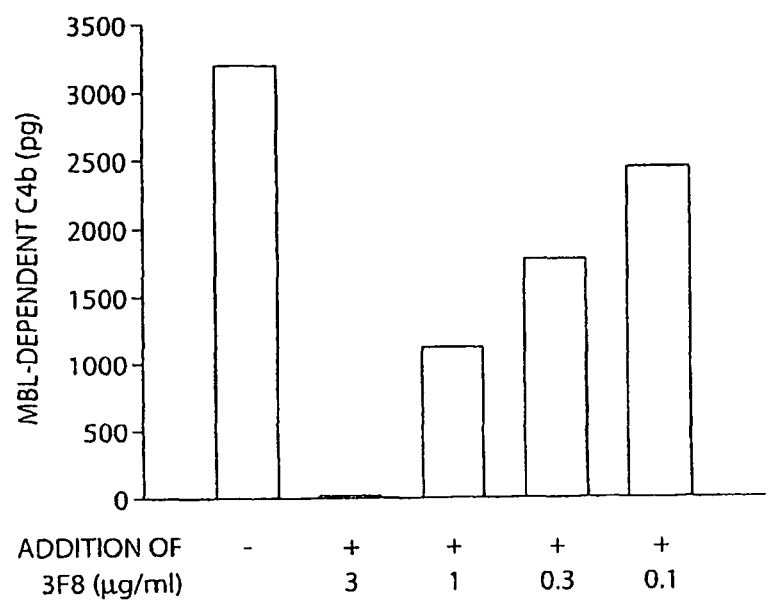
Figure 8D:
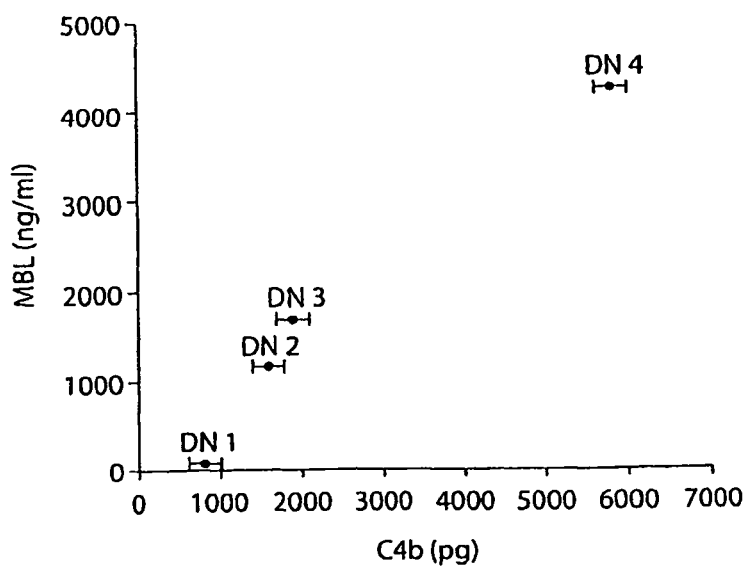

A linear correlation between detected units of integrated intensity (II) at 800 nm using known amounts of C4b plated onto 384 well plates is shown in FIG. 8A. Using the data obtained from FIG. 8A, the amount of MBL-dependent C4b that was bound to the mannan coated plates was then determined following incubation of the PLS. As shown in FIG. 8B a log-linear relationship between the integrated intensity of activated PLS deposited C4b and known amounts of C4b was observed. These data were used to standardize the PLS and its ability to deposit known amounts of C4b onto mannan-coated plates. Specificity for MBL-dependent C4b deposition was further verified by the ability of mAb 3F8 to dose-dependently inhibit C4b deposition (FIG. 8C). Serum samples prepared in the previous step for MBL analysis (FIG. 7C, DN1-4) were further evaluated in the same well for MBL-dependent C4b deposition against the PLS using a log-linear regression fit and expressed as MBL-dependent C4b in pg (FIG. 8D).

The classical/lectin C3 convertase, C4b2a, is formed by MBL/MASP-2 cleavage of complement protein C2, concurrent with C4 cleavage and deposition of C4b (FIG. 5). Formation of the C3 convertase demonstrates the capacity of the MBL-dependent LCP to activate the complement cascade once MBL binds to its target ligand. Thus, C3b deposition signifies formation of a functional C3 convertase and as such indirectly allows for evaluation of functional. C2 in a sera/plasma sample (FIG. 5). The dual channel technology of this LCP assay allows for the multiplicity of endpoint evaluation using the 700 nm channel to assess MBL-dependent C3 convertase activity by observation of C3b deposition onto the mannan coated plate.

Figure 9A:
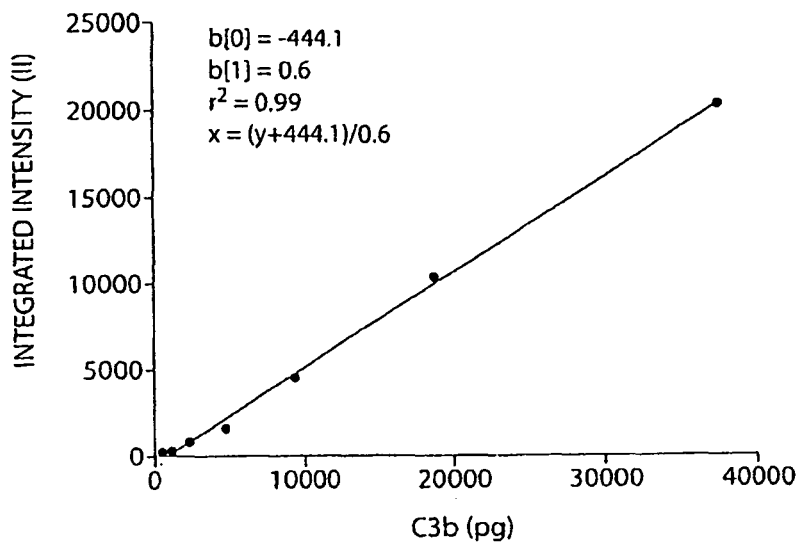
FIG. 9 illustrates quantitation of MBL-dependent C3b deposition. A linear correlation between detected units of integrated intensity (II) at 700 nm using known amounts of C3b plated onto 384 well plates was established (FIG. 9A). The amount of MBL-dependent C3b that was bound to the mannan-coated plates following incubation of the PLS was revealed as a log-linear relationship between the integrated intensity of activated PLS deposited C3b and known amounts of C3b (FIG. 9B). Specificity for MBL-dependent C3b deposition was verified by inhibition with mAb 3F8 (FIG. 9C). Using the PLS to establish MBL-dependent C3b levels, triplicate values of each donor (DN 1=donor 1, DN 2=donor 2, DN 3=donor 3, DN 4=donor 4) serum sample diluted in binding buffer are expressed as mean+/−SE of the PLS for C3b (horizontal bars) and MBL (vertical bars).
Figure 9B:
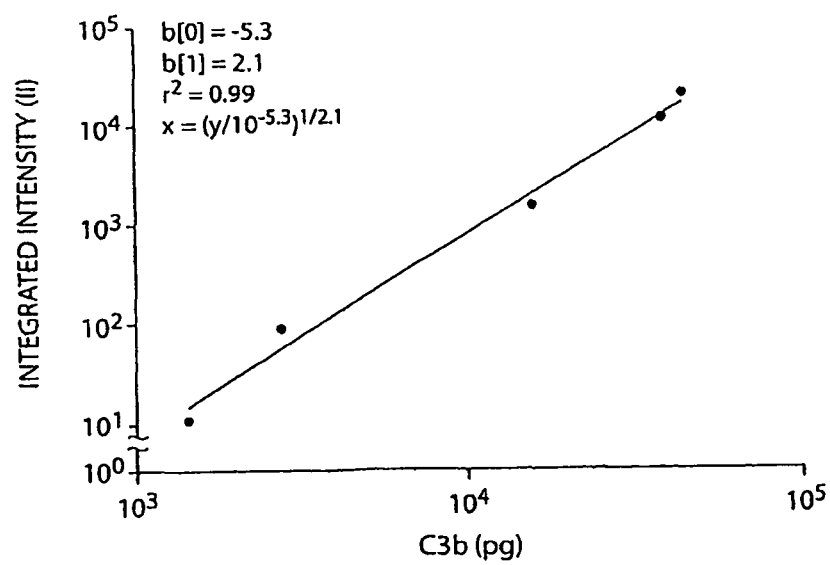
Figure 9C:
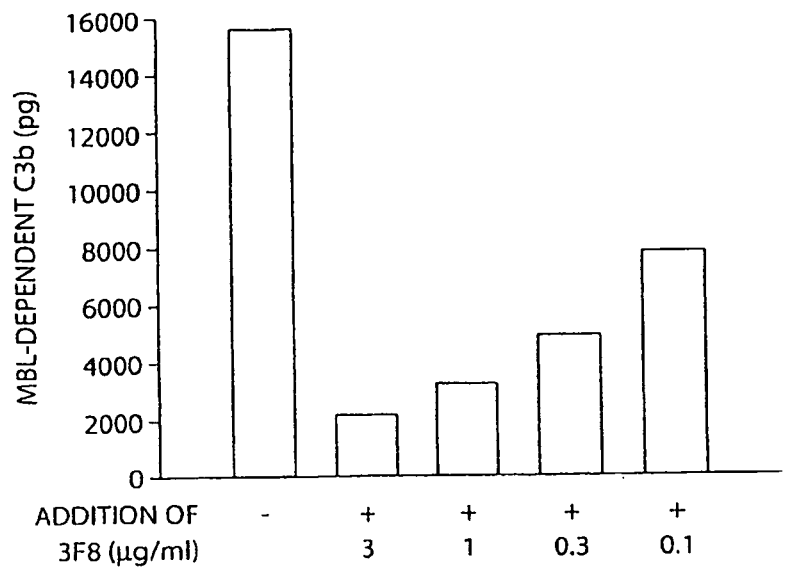
Figure 9D:
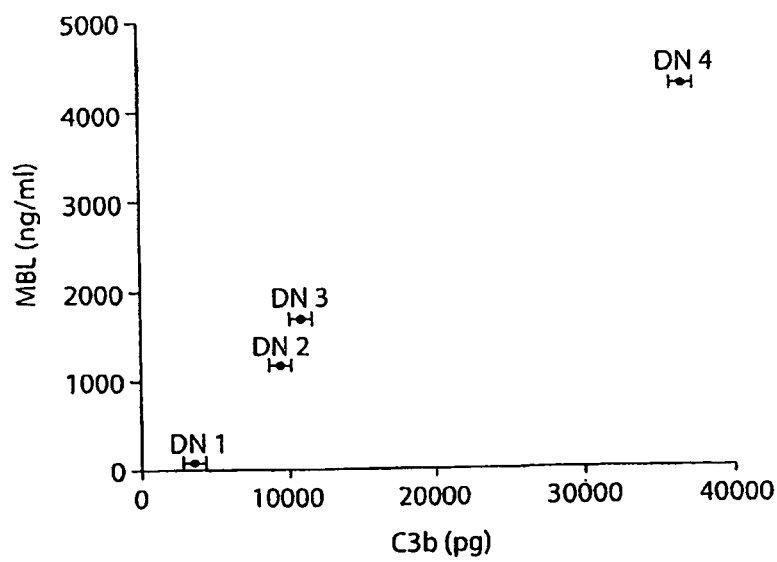

Similar to the methods used for the standardization for C4b, known amounts of C3b were plated onto 384 well plates. A linear correlation between detected units of integrated intensity (II) at 700 nm using known amounts of C3b plated to 384 well plates is shown in FIG. 9A. Using the data obtained the amount of MBL-dependent C3b that was bound to the mannan coated plates was then determined following-incubation of the PLS. As shown in FIG. 9B a log-linear relationship between the integrated intensity of activated PLS deposited C3b and known amounts of C3b were observed. These data were used to standardize the PLS and its ability to deposit-known amounts of, C3b onto mannan-coated plates. Intra-assay-coefficient variation was 10%. Specificity for MBL-dependent C3b deposition was further verified by the ability of mAb 3F8 to dose-dependently inhibit C3b deposition (FIG. 9C). Serum samples prepared in the previous step for MBL analysis (FIG. 3C, DN 1-4) and C4b analysis (FIG. 8D) were further evaluated in the same well for MBL-dependent C3b deposition against the PLS using a log-linear regression fit and expressed as MBL-dependent C3b in pg (FIG. 9D).

Figure 10A:
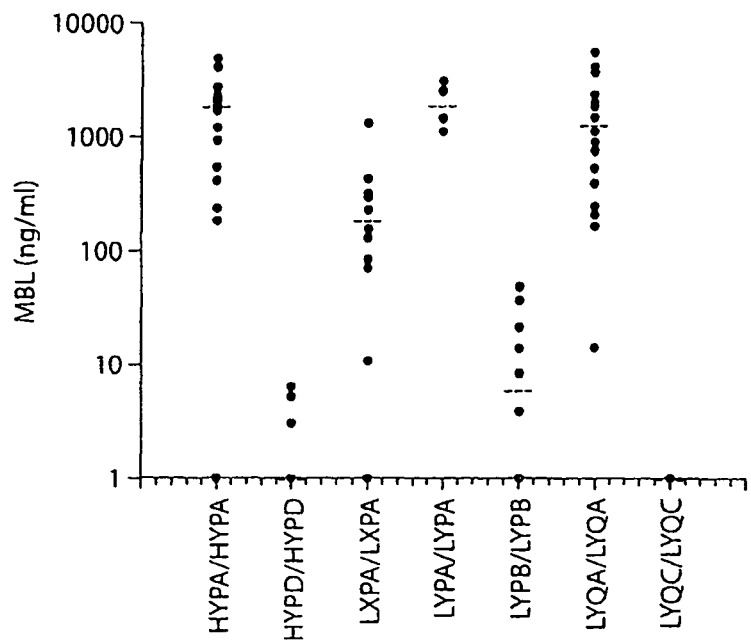
FIG. 10 provides results from an analysis of functional MBL, and MBL-dependent LCP activation, correlated to MBL genotype. Serum samples from donors with the indicated MBL haplotype were evaluated for functional MBL (FIG. 10A), C4b deposition (FIG. 10B) and C3b deposition (FIG. 10C). Differences between medians of haplotype groups for MBL, MBL-dependent C4b, and MBL-dependent C3b are statistically significant; Kruskal-Wallis ANOVA on ranks ($p<0.001$). There is a direct correlation to functional MBL concentrations with C4b deposition (FIG. 10D) and C3b deposition (FIG. 10E). The MBL-dependent LCP phenotype can be summarized by evaluating MBL binding, MBL-dependent C4b and C3b deposition together (FIG. 10F).
Figure 10B:
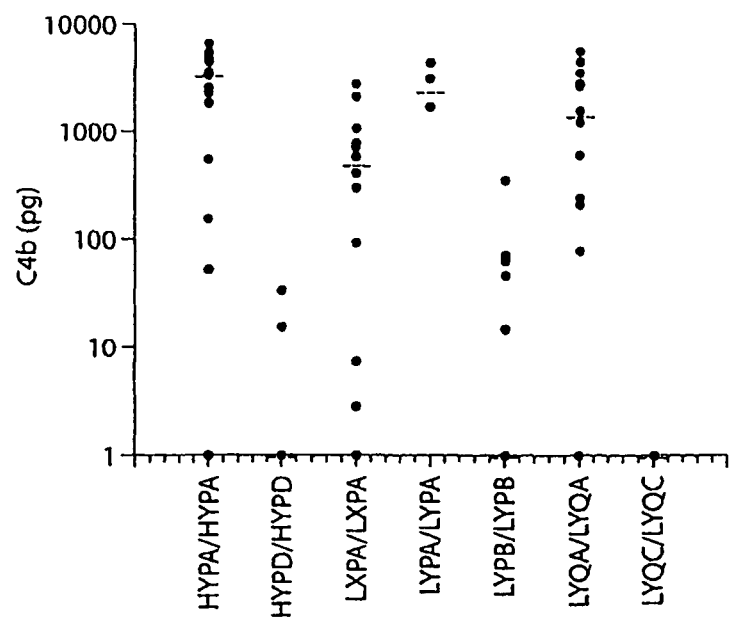
Figure 10C:
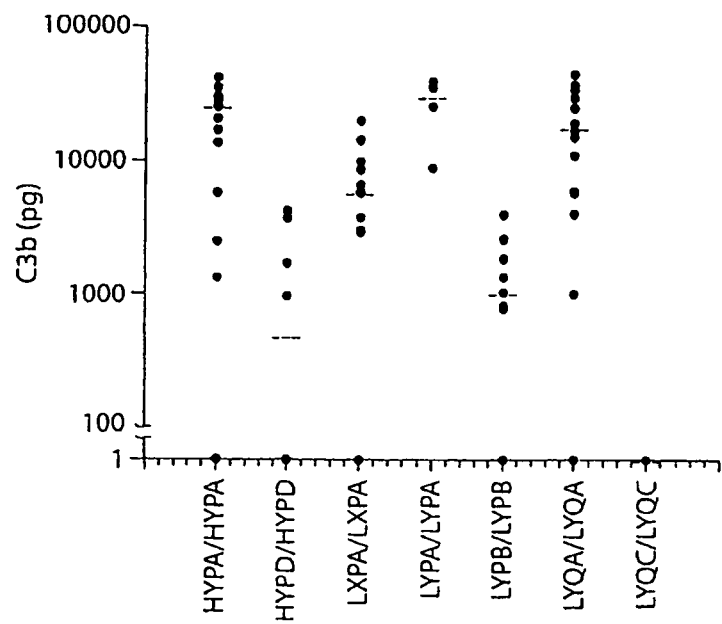
Figure 10D:
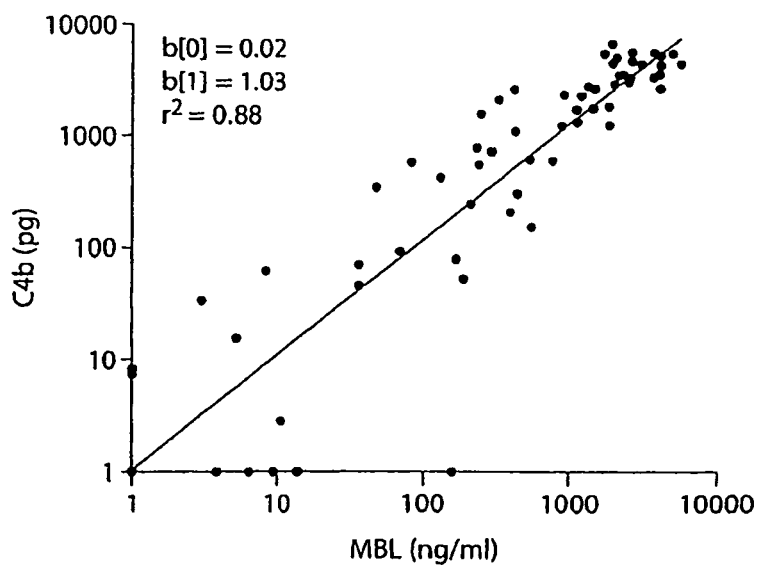
Figure 10E:
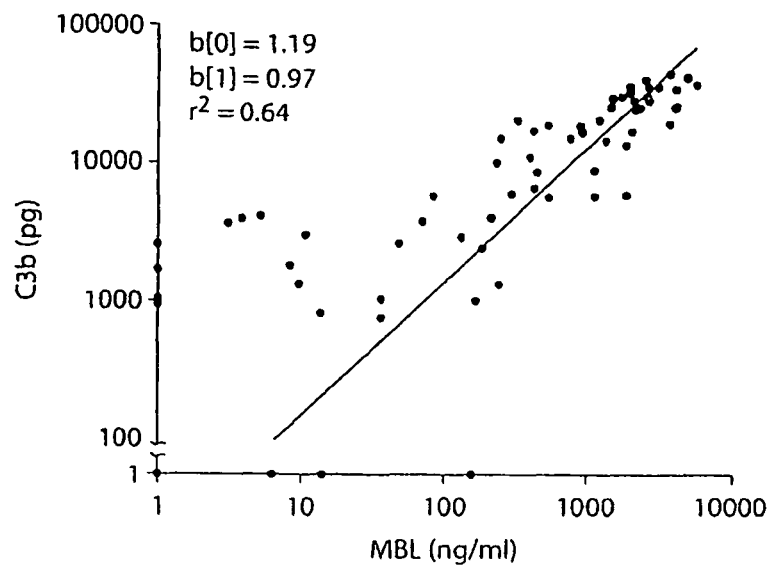
Figure 10F:
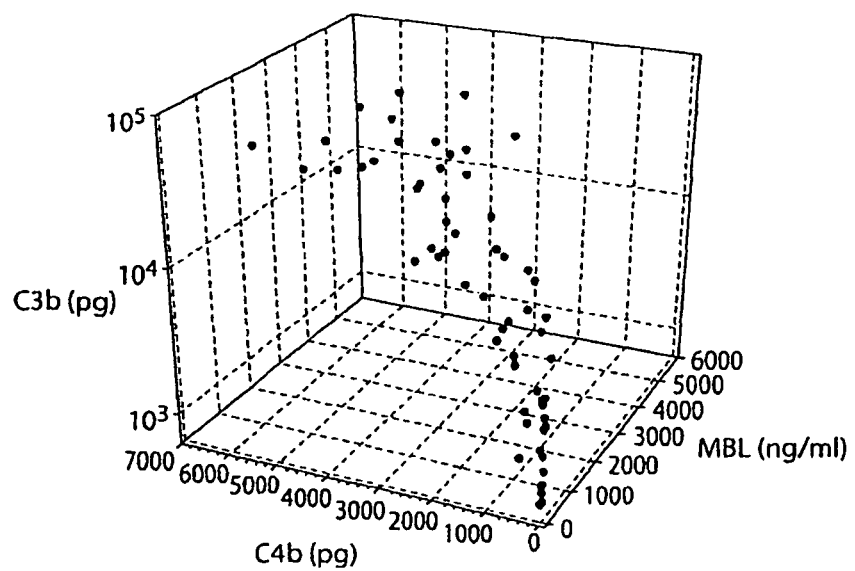

To confirm the precision of this MBL-dependent LCP assay, donors of known MBL haplotype (Table. 1) representing a broad range of functional MBL expression were analyzed for MBL and MBL-dependent C4b and C3b deposition. As observed in FIG. 10A measurement of functional MBL confirms the previously reported levels of functional MBL observed in these haplotypes (Steffensen et al., 2000; Terai et al., 2003). Expanding upon these past observations, the MBL-dependent LCP activation and subsequent C4b (FIG. 10B) and C3b (FIG. 10C) deposition associated with these known MBL-haplotypes are quantified using this novel assay system. Activation of the LCP by the functional MBL complex (e.g., functional MASP-2) reveals a quantifiable direct-proportional increase of functional MBL binding and C4b deposition (FIG. 10D). The capacity for these various MBL haplotypes to also deposit C3b is shown. A quantifiable proportional increase of functional MBL binding and C3b deposition was observed (FIG. 10E). The MBL-dependent LCP phenotype can be summarized by evaluating MBL binding, MBL-dependent C4b and C3b deposition together (FIG. 10F). This 3D graph demonstrates that functional MBL, dictated by individual MBL haplotypes, appears to drive the activation and deposition of effector LCP components.

TABLE 1

Represented MBL Haplotypes

| Haplotype (Homozygotes) | Previously Reported MBL (ng/ml)* | MBL-LCP Assay MBL (ng/ml) | n | SE |
|---|---|---|---|---|
| HYPA/HYPA | 2003 (n = 54) | 2028 | 18 | 364 |
| HYPD/HYPD | 61 (n = 1) | 2 | 9 | 1 |
| LXPA/LXPA | 118 (n = 4) | 292 | 12 | 104 |
| LYPA/LYPA | 1738 (n = 2) | 2053 | 4 | 461 |
| LYPB/LYPB | 22 (n = 2) | 13 | 12 | 5 |
| LYQA/LYQA | 1899 (n = 5) | 1739 | 18 | 383 |
| LYQC/LYQC | 0 | 0 | 3 | 0 |

*from R. Steffensen et al., Journal of Immunological Methods 241 (2000) 33-42 and Terai et., al Eur. J. Imm. 33 (2003) 2755-2763

Figure 11A:
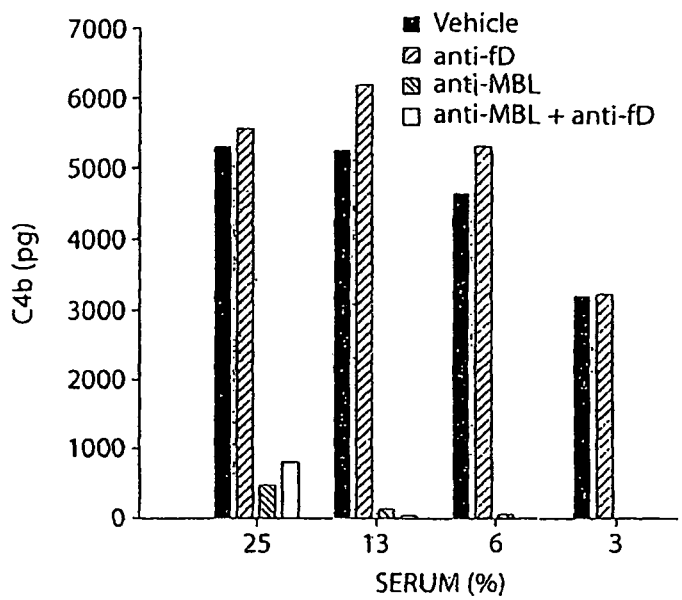
FIG. 11 provides results from an analysis of MBL-dependent AP amplification. MBL-dependent C4b deposition evaluated in 3-25% sera is inhibited by 3F8 and not anti-factor D (FIG. 11A). Alternatively, MBL-dependent AP 'tick over' amplification occurs approaching physiologic serum concentration (13 and 25%), as anti-human MBL mAb 3F8 together with anti-human factor D mAb can inhibit C3b deposition (FIG. 11B), but neither of these mAb can completely inhibit independently. Analysis of MBL-dependent AP amplification at 25% serum shows that although MBL-dependent C4b deposition remains compromised in DN1 (MBL-low/deficient) compared to DN 4 (MBL-high) (FIG. 11C), deficiency in MBL-dependent LCP activation can be rescued at the level of C3 convertases (FIG. 11D) when DN 1 is compared with DN 4 at 25% sera concentration.
Figure 11B:
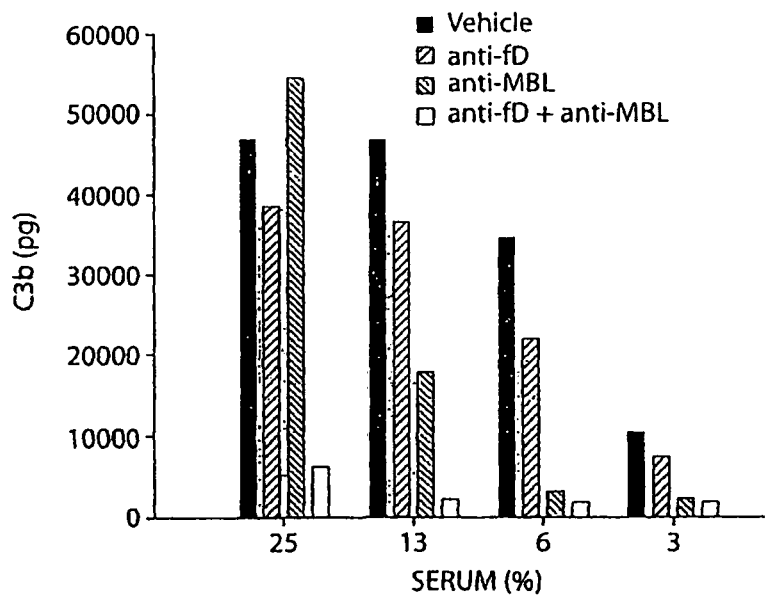
Figure 11C:
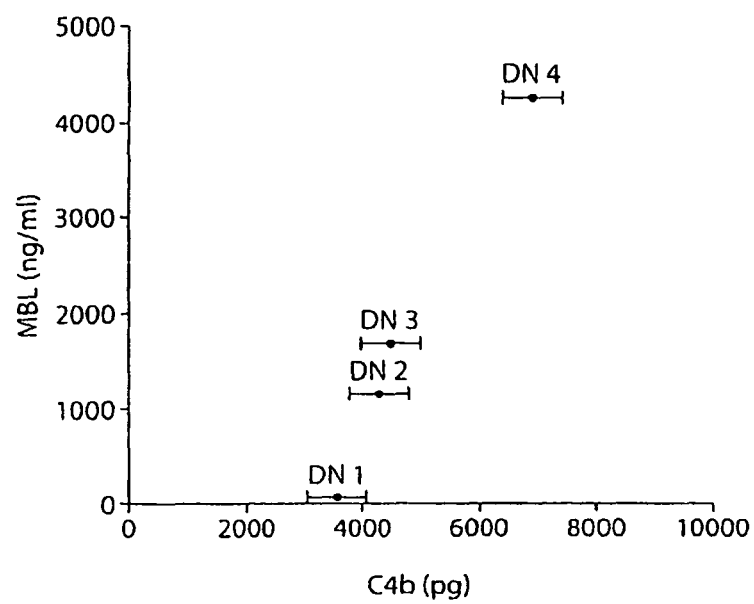
Figure 11D:
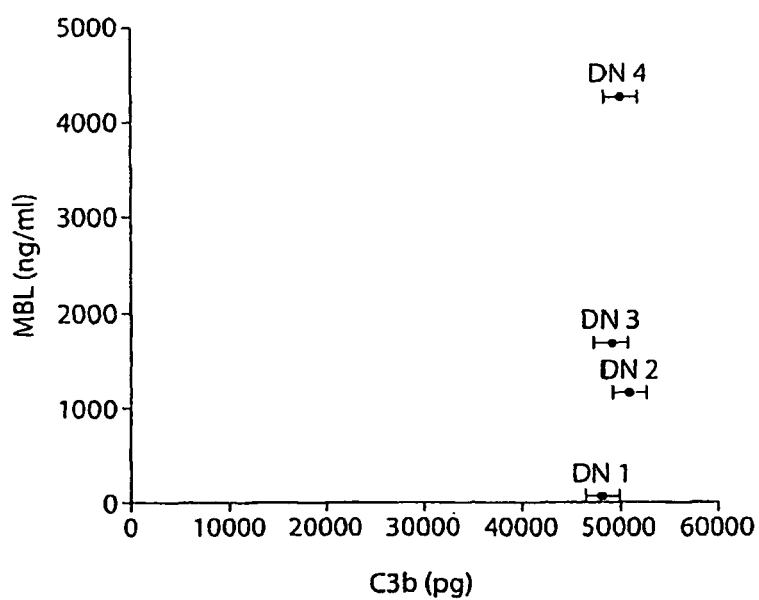
Figure 12:
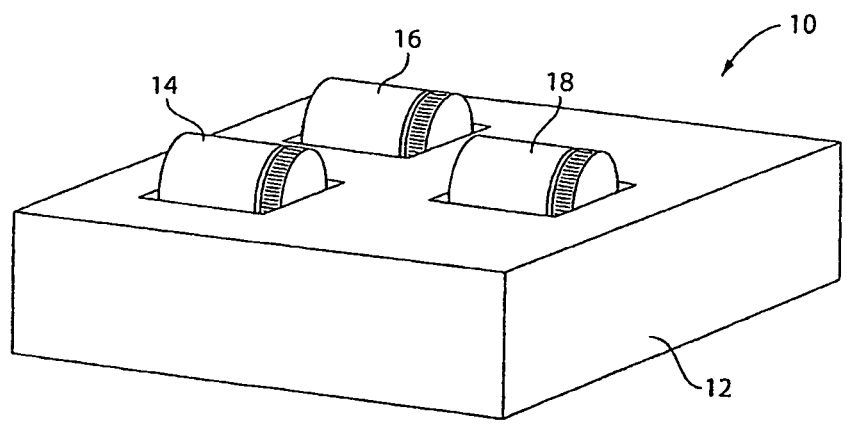
Fig. 12 illustrates an example of a kit. Item 10 provides the kit. Item 12 provides a kit structure. Items 14, 16 and 18 each represent a container in the kit.

A proposed interaction of MBL with the alternative pathway (AP) has been evaluated (Selander-et al., 2006). Further, the AP mediated amplification of optimal MBL-dependent LCP-opsinophagocytosis has been demonstrated (Brouwer et al., 2006). C4b and C3b deposition in this assay at 3-25% sera concentrations was evaluated (FIG. 11). As shown in FIG. 11A, C4b deposition is entirely dependent on MBL, as inhibition of MBL with mAb 3F8, but not inhibition of factor D, completely inhibits C4b deposition at all the sera-concentrations evaluated. In contrast, C3b deposition (FIG. 11B) at 13% and 25% sera is dependent on the interactions of MBL and the alternative pathway, as inhibition of MBL (3F8) and factor D (anti-fD) completely inhibited C3b deposition, whereas inhibition of each of these two molecules individually was ineffective. At sera concentrations of 3% and 6%, inhibition of MBL, but not factor D effectively inhibited C3b deposition. Interestingly, in an MBL-deficient (low) donor (DN1), it is clear that MBL-dependent LCP activation (e.g., C4b and C3b deposition) is compromised in comparison to MBL-normal or high expressers (FIG. 8D and FIG. 9D). However, evaluating this same donor in the window of MBL-dependent AP amplification; it is clear that C4b deposition remains relatively compromised (FIG. 8D vs. FIG. 11C) yet C3b deposition recovers to MBL-normal levels (FIG. 9D vs. FIG. 11D). Thus, this assay addresses a potential role of the MBL-dependent pathway to interact with the alternative pathway to increase C3b deposition in MBL-deficient or MBL-low expresser patients.

Plasma samples were also taken from the same individuals (n=3) and subjected to the FLISA as described. While there was a tendency to have higher values for each of the measured parameters, no significant difference was observed (mean±SEM). These data (Table 2) demonstrate that plasma (citrate and likely EDTA or heparin containing clinical sample tubes) can also be used to assay the LCP after recalcification.

TABLE 2

Comparison of plasma and sera samples

|  | MBL (ng/ml) | C4b (pg) | C3b (pg) |
|---|---|---|---|
| Sera | 1505 ± 418 | 2797 ± 1417 | 10302 ± 4351 |
| Plasma | 2732 ± 576 | 3552 ± 619 | 21325 ± 6791 |

Sera samples were collected from four individuals and run in the FLISA as fresh samples or frozen to −80° C. and thawed to room temperature five times and then run again in the FLISA. Data (Table 3) are means ±SEM for n=4 determinations. No significant differences were observed for MBL, C4b or C3b at any of the individual points. These data demonstrate that frozen samples can be used from established databases or frozen and analyzed at a later date without significant loss information obtained in the frozen/thawed samples.

TABLE 3

Freeze/thaw data

| Fresh | 1 | 2 | 3 | 4 | 5 |
|---|---|---|---|---|---|
| MBL(ng/ml) | | | | | |
| 1418 ± 314 | 1344 ± 333 | 1239 ± 269 | 1635 ± 436 | 1431 ± 395 | 1424 ± 265 |
| C4b (pg) | | | | | |
| 3118 ± 935 | 2469 ± 911 | 2337 ± 776 | 1562 ± 547 | 2713 ± 1102 | 2828 ± 1031 |
| C3b(pg) | | | | | |
| 33800 ± 2551 | 32836 ± 2844 | 34424 ± 3556 | 34408 ± 3601 | 34379 ± 3300 | 32906 ± 3326 |

Discussion

Described herein are assays that include assays that detect the functional status of the LCP utilizing a high-throughput liquid handling system, together with infra-red technology, examples of which are described in the foregoing example and about which the following discussion pertains.

This is the first multi-tiered LCP assay prototype that can successfully analyze the key components of early LCP activation from a single sample. This analysis can be performed for both serum samples and plasma samples. Importantly, the prototype for this multi-endpoint LCP assay demonstrates the shortcomings of currently available assays for analyzing MBL-dependent LCP activation in patient samples, while highlighting the ability of this platform to overcome these challenges. Dual channel detection (FIG. 6C), together with the application of a regeneration buffer (FIG. 6B), allows re-establishment of an evaluation platform to analyze comprehensively the functional capabilities of an individual's LCP. In addition, evaluation can be performed in a single, small volume sample of serum or plasma, making the assay quick and cost efficient. A complete LCP pathway evaluation has yet to be demonstrated in currently available assays, which require additional sample and evaluation of additional endpoints (C4 or C3) in separate experimental steps (Roos et al., 2003), or additional sample and reconstitution with exogenous C4 (Petersen et al.; 2000; Petersen et al., 2001). Evaluation of the LCP in these previously published assays does not represent the physiological contributions of the patient's own C4, including interaction with MASP-2 (Rossi et al.; 2001; Rossi et al., 2005), formation of the C3 convertase, and subsequent C3 activation and deposition.

The example assay reports functional MBL, MBL-dependent C4b, and MBL-dependent C3b activation and deposition in plasma or serum using a pooled serum standard (PLS). The PLS was batched, aliquoted and assigned a lot designation thereby establishing intra-assay consistency as reported in Materials and Methods. A common PLS for multiple endpoint analysis adds to the already efficient and cost-effective analysis platform by essentially combining three individual protein standards into one. The PLS is specific for MBL (FIG. 7), MBL-dependent C4 activation (FIG. 8), and formation of MBL-dependent C3 convertase (FIG. 9), as the anti-MBL mAb 3F8 can abrogate MBL binding and the subsequent C4b and C3b deposition. The PLS was also evaluated against a standard serum control commonly used in other MBL assay protocols, and independently confirmed the functional MBL content as 1 µg/ml.

It is clear that MBL is important clinically as lower levels of MBL predispose certain patients to recurrent infection (Zhang et al., 2005; Bathum et al., 2006), while progressively higher levels of MBL have been associated with post-surgical complications including ischemia/reperfusion (i/R) injury, coronary diseases and more recently, diabetes (Fiane et al., 2003; Best et al., 2004; Saevarsdottir et al., 2005; Bouwman et al., 2005). Functional MBL levels are dictated by a group of SNPs; the most highly represented haplotypes associated with the promoter, the structural gene segment, and the untranslated region affecting both overall production (Madsen et al., 1995) and/or stability and function of the circulating MBL multimer (Dean et al., 2006). Available assay techniques have correlated functional MBL in ng/ml to patient haplotype, therefore a representative panel of MBL haplotypes (Table 1) was selected and evaluated for functional MBL in confirmation of the described MBL-dependent LCP FLISA (FIG. 10A). Evaluated MBL levels were within the standard error of the means (SE) of the previously reported values as indicated in Table 1.

Importantly, the assay is able to take MBL-dependent evaluation further than previously possible, establishing an MBL-dependent LCP activity phenotype including circulating functional MBL, and downstream MBL-dependent LCP activation. For example, multiple MASP-2 SNPs have been identified, and associated with disease prevalence including colorectal cancer and esophageal squamous cell carcinoma (Verma et al., 2006; Sjoholm et al., 2006). Circulating levels of MASP-2 have been evaluated using a sandwich ELISA, although functional levels of MASP-2 in patient samples have yet to be evaluated (Moller-Kristensen et al., 2003). The example MBL-dependent LCP FLISA evaluates functional MASP-2 activity via C4b deposition, as the MBL/MASP-2 complex is required for LCP complement cascade activation through enzymatic cleavage of C4. Recent analysis of MASP-2 SNPs confirmed that functional MASP-2 is required for activation and deposition of C4b, yet the level of C4-activation and C4b deposition may be driven more by functional MBL and not variant MASP-2 (Teillet et al., 2005). As seen in FIG. 8D and FIG. 11D, there is a direct correlation with C4b deposition and circulating functional MBL. The MBL dependent deposition of C4b has been demonstrated previously (Petersen et al., 2001), and although, associated with MBL haplotype (Roos et al., 2003), the magnitude of MBL-dependent activation was not quantified. A quantifiable evaluation of MBL/MASP-2 activation is shown herein.

There is the possibility that C4b deposition in the FLISA could be limited by a hereditary C4 deficiency, and not functional MASP-2-capacity. Complete deficiency of C4 is well documented, although rare, and linked to SLE, membranoproliferative glomerulonephritis, and chronic angioedema (Fishelson et al., 2001; Azofra and Lopez-Trascasa, 2001; Suzuki et al., 2003; Yang et al., 2004; Lhotta et al.; 2004; Sjoholm et al., 2006). Addition of exogenous C4 to a C4b-deposition negative patient sample (Petersen et al., 2000; Petersen et al., 2001), and performing a second evaluation for MBL/MASP-2 dependent C4b deposition would address this issue. Alternatively, functional and quantitative MASP-2 levels may be evaluated independently as a fourth endpoint using an anti-MASP-2 mAb.

The enzymatic activation of C4 by the MBL/MASP-2 initiation complex leads to formation of the classical C3 convertase. Together with C2, C4b2a cleaves C3 into the fluid phase C3a anaphylotoxin and the covalently bound opsonin, C3b (Walport, 2001a; Walport, 2001b). Formation of the C3 convertase is important to the propagation of the LCP enzymatic cascade resulting in clearance of infectious pathogens via opsinophagocytosis, and lytic clearance via the terminal complement complex (TCC, C5b-9). In sterile inflammation, formation of the C3 convertase and C3 cleavage is associated with complement-dependent ischemia and reperfusion injury (Weisman et al., 1990; Souza et al., 2005) and cardiopulmonary bypass (De Silva et al., 2006), IgA nephropathy (Gherghiceanu et al., 2005) and allograft survival (Brown et al., 2006). Interestingly, it has been suggested that restenosis following endarterectomy correlates with high functional MBL (MBL2 haplotype A/A individuals), and increased circulating-C3 (Szeplaki et al., 2006). Evaluation of comprehensive MBL-dependent complement activation at the level of C3 demonstrates a direct correlation of circulating MBL and C3b deposition (FIG. 9D). Furthermore, MBL-dependent C3b deposition proportionally correlates to functional MBL haplotypes (FIG. 10C) further describing what was defined above as an MBL-dependent activation phenotype. It remains to be seen whether this MBL/LCP phenotype is driven by other components of the MBL-dependent LCP in addition to MBL. However, as with activation and deposition of C4, there seems to be a direct correlation of C3 activation and deposition with circulating MBL (FIG. 10E). As described earlier for the MBL/MASP-2 complex activation capacity at the level of C4, MBL-dependent C3 convertase formation is quantifiable.

Similar to C4, there is the possibility that C3b deposition is limited by a hereditary C3 deficiency, or potentially C2 deficiency. The incidence of C3 deficiency is unclear, although clinically, primary C3 deficient patients present with severe infections, and often in early childhood (Reis et al., 2006a). Deficiencies in C3 have also been linked to SLE and membranoproliferative glomerulonephritis (Borzy et al., 1988; Da Silva et al., 2002; Reis et al., 2006b). Alternatively, C2 deficiency is a very common inherited complement deficiency, with an incidence reported at 1:20,000 (Sjoholm et al., 2006). Patients deficient in C2 can be asymptomatic, but may present with SLID or discoid lupus, and increased systemic infections with encapsulated bacteria (Sjoholm et al., 2006). Augmenting a MBL-dependent C3b-deposition negative sample with C3, would likely address which deficiency (i.e., C2 or C3) was involved. In the case of C2 deficiency, addition of C3 to the patient sample would remain C3b-deposition negative as the convertase is not able to form. However, in a C3 deficient patient, addition of C3 to the sample would restore the substrate to the functionally active convertase, resulting in C3b deposition.

Other assay platforms evaluating MBL-dependent C3 activation have looked at MBL-dependent AP amplification or a 'bypass' pathway of MBL/C3 interaction (Selander et al., 2006; Brouwer et al., 2006), although MBL-dependent C3 activation was not quantitated in either assay. In addition to the direct evaluation of MBL-specific LCP activation, the FLISA can address the mechanisms of alternate MBL-dependent complement activation proposed (Selander et al., 2006; Brouwer et al., 2006). It is clear that direct MBL-dependent C4b2a activation of the LCP is driven by functional MBL as shown in FIGS. 10 and 11, and as published (Selander et al.; 2006). However, as shown in FIG. 11D, the capacity for MBL-dependent AP amplification may drive the potential for downstream complement activation at the level of C3 convertases with respect to MBL deficient or 'low' expressers. The definition of MBL deficiency in the literature is controversial, as some report MBL-deficiency as <50 ng/ml-(Christiansen et al., 1999), <100 ng/ml (Gadjeva et al., 2004) or <500 ng/ml (Ytting et al., 2005; Frederiksen et al., 2006) functional MBL protein. However, one group used <1000 ng/ml as their plateau for correlative MBL deficiency (Neth et al., 2001). With the potential to form even small amounts of C3 convertase, 'tick-over' amplification may salvage otherwise limited MBL-dependent LCP capacity during various immunologic challenges. Similarly, a 'bypass' mechanism may achieve the same end via different means (Selander et al., 2006). The distinction between the two surrogate MBL-dependent activation routes may be driven by the components of the complement component arsenal unique to each sample (i.e., the relatively common occurrence of C2 deficiency). Furthermore, differential MBL-ligand recognition may play a role in surrogate MBL-dependent complement activation, as a recent evaluation of MBL-dependent/C2-independent C3 activation showed a preference for O-linked mannose in serogroup C(CO) of *Salmonella* over other mannose-containing serotypes DO and BO (Selander et al., 2006).

An additional member of the lectin family are the ficolins, which recognize and activate the LCP through shared MASPs (Matsushita et al., 2000) as shown in FIG. 5. As it is becoming increasing clear that ficolins may play an important role in human disease, evaluation of ficolin-dependent LCP activation is necessary. Incidence of ficolin deficiency in the general population remains unclear, as does the potential for self-antigen recognition by ficolins. A recent study of gastrointestinal I/R and secondary lung injury showed neutrophil infiltration and C3 deposition independent of MBL or C1q yet dependent on C2 (Hart et al., 2005). As primary injury in this model was MBL-dependent, this lead to the speculation that ficolins played a role in mediating auto-epitope recognition and secondary I/R damage. The versatility of this assay platform allows for the modification of the protocol and evaluation of the contribution of the ficolin-LCP using an alternate functional target (GlcNAc) and antibodies directed towards L-, H- and/or M-ficolins.

The MBL-dependent LCP FLISA extends what is currently understood about functional MBL by describing quantitatively the MBL-dependent LCP activation to the level of C3 convertases. Furthermore, it has been demonstrated that MBL-dependent LCP activation is influenced by the MBL genotype. Because the MBL haplotype alters LCP activation through cleavage and deposition of C3b, an analysis of MBL-dependent complement activation in a MBL-dependent LCP activation phenotype in a single assay is described. This analysis includes the evaluation of MBL-dependent AP amplification, which may play a role in otherwise low MBL expresser individuals. This mechanism of MBL-dependent salvage should be considered with respect to the selective pressure that retaining a high frequency of MBL2 mutation in the population. MBL-deficient/low patients may be protected when it comes to self-antigen recognition following sterile challenge (i.e., I/R injury), yet MBL-dependent AP amplification may impart protection to MBL-deficient individuals by 'alternatively' activating the LCP following pathogenic challenge. Utilization of a MBL-dependent LCP. FLISA to evaluate clinical samples collected from donors in differing compromised populations will further the understanding of LCP activation in both infectious and sterile inflammation and injury.

References for Example 2

1. Azofra, J. and Lopez-Trascasa, M., 2001. C4 deficiency in chronic angioedema. Allergy 56, 1106.
2. Baccarelli, A., Hou, L., Chen, J., Lissowska, J., El-Omar, E. M., Grillo, P., Giacomini, S. M., Yaeger, M., Bernig, T., Zatonski, W., Fraumeni, J. F., Jr., Chanock, S. J. and Chow, W. H., 2006. Mannose-binding lectin-2 genetic variation and stomach cancer risk. Int. J. Cancer.
3. Bathum, L., Hansen, H., Teisner, B., Koch, C., Garred, P., Rasmussen, K. and Wang, P., 2006. Association between combined properdin and mannose-binding lectin deficiency and infection with Neisseria meningitidis. Mol. Immunol. 43, 473.
4. Bax, W. A., Cluysenaer, O. J., Bartelink, A. K., Aerts, P. C., Ezekowitz, R. A. and van, D. H., 1999. Association of familial deficiency of mannose-binding lectin and meningococcal disease. Lancet 354, 1094.
5. Best, L. G., Davidson, M., North, K. E., MacCluer, J. W., Zhang, Y., Lee, E. T., Howard, B. V., DeCroo, S. and Ferrell, R. E., 2004. Prospective analysis of mannose-binding lectin genotypes and coronary artery disease in American Indians: the Strong Heart Study. Circulation 109, 471.
6. Borzy, M. S., Gewurz, A., Wolff, L., Houghton, D. and Lovrien, E., 1988. Inherited C3 deficiency with recurrent infections and glomerulonephritis. Am. J. Dis. Child 142, 79.
7. Bouwman, L. H., Eerligh, P., Terpstra, O. T., Daha, M. K., de, K. P., Ballieux, E., Bruining, G. J., van der Slik, A. R., Roos, A. and Roep, B. O., 2005. Elevated levels of mannose-binding lectin at clinical manifestation of type 1 diabetes in juveniles. Diabetes 54, 3002.
8. Brouwer, N., Dolman, K. M., van, Z. R., Nieuwenhuys, E., Hart, M., Aarden, L. A., Roos, D. and Kuijpers, T. W., 2006. Mannan-binding lectin (MBL)-mediated opsonization is enhanced by the alternative pathway amplification loop, Mol. Immunol. 43, 2051.
9. Brown, K. M., Kondeatis, E., Vaughan, R. W., Kon, S. P., Farmer, C. K., Taylor, J. D., He, X., Johnston, A., Horsfield, C., Janssen, B. J., Gros, P., Zhou, W., Sacks, S. H. and Sheerin, N. S.; 2006. Influence of donor C3 allotype on late renal-transplantation outcome. N. Engl. J. Med. 354, 2014.
10. Burton, D. R. and Dwek, R. A., 2006. Immunology. Sugar determines antibody activity. Science 313, 627.
11. Calvo-Alen, J., Alarcon, G. S., Tew, M. B., Tan, F. K., McGwin, G., Jr., Fessler, B. J., Vila, L. M. and Reveille, J. D., 2006. Systemic lupus erythematosus in a multiethnic US cohort: XXXIV. Deficient mannose-binding lectin exon 1 polymorphisms are associated with cerebrovascular but not with other arterial thrombotic events. Arthritis Rheum. 54, 1940.
12. Cedzynski, M., Szemraj, J., Swierzko, A. S., Bak-Romaniszyn, L., Banasik, M., Zeman, K. and Kilpatrick, D. C., 2004. Mannan-binding lectin insufficiency in children with recurrent infections of the respiratory system. Clin. Exp. Immunol. 136, 304.
13. Christiansen, O. B., Kilpatrick, D. C., Souter, V., Varming, K., Thiel, S, and Jensenius, J. C., 1999. Mannan-binding lectin deficiency is associated with unexplained recurrent miscarriage. Scand. J. Immunol. 49, 193.
14. Collard, C. D., Vakeva, A., Morrissey, M. A., Agah, A., Rollins, S. A., Reenstra, W. R., Buras, J. A., Meri, S. and Stahl, G. L., 2000. Complement activation after oxidative stress: role of the lectin complement pathway. Am. J. Pathol. 1.56, 1549.
15. Da Silva, R. E., Baracho, G. V., Sousa, L. A., Farah, C. S. and Isaac, L., 2002. Homozygous hereditary C3 deficiency due to a premature stop codon. J. Clin. Immunol. 22, 321.
16. De Silva, R. J., Vuylsteke, A., Fritchley, S. J., Trull, A. K., Dunning, J. J. and Wallwork, J, 2006. APT070 inhibits complement activation during in vitro cardiopulmonary bypass. Eur. J. Cardiothorac. Surg. 30, 72.
17. Dean, M. M., Heatley, S. and Minchinton, R. M., 2006. Heteroligomeric forms of codon 54 mannose binding lectin (MBL) in circulation demonstrate reduced in vitro function. Mol. Immunol. 43, 950.
18. Endo, M., Ohi, H., Ohsawa, I., Fujita, T., Matsushita, M. and Fujita, T., 1998. Glomerular deposition of mannose-binding lectin (MBL) indicates a novel mechanism of complement activation in IgA nephropathy. Nephrol. Dial. Transplant. 13, 1984.
19. Fiane, A. E., Videm, V., Lingaas, P. S., Heggelund, L., Nielsen, E. W., Geiran, O. R., Fung, M. and Mollnes, T. E., 2003. Mechanism of complement activation and its role in the inflammatory response after thoracoabdominal aortic aneurysm repair. Circulation 108, 849.
20. Fishelson, Z., Attali, G. and Mevorach, D., 2001. Complement and apoptosis. Mol. Immunol. 38, 207.
21. Font, J., Ramos-Casals, M., Brito-Zeron, P., Nardi, N., Ibanez, A., Suarez, B., Jimenez, S., Tassies, D., Garcia-Criado, A., Ros, E., Sentis, J., Reverter, J. C. and Lozano, F., 2006. Association of mannose-binding lectin gene polymorphisms with antiphospholipid syndrome, cardiovascular disease and chronic damage in patients with systemic lupus erythematosus. Rheumatology (Oxford).
22. Frederiksen, P. D., Thiel, S., Jensen, L., Hansen, A. G., Matthiesen F. and Jensenius, J. C., 2006. Quantification of mannan-binding lectin. J. Immunol. Methods 315, 49.
23. Gadjeva, M., Takahashi, K. and Thiel, S., 2004. Mannan-binding lectin—a soluble pattern recognition molecule. Mol. Immunol. 41, 113.
24. Garred, P., Madsen, H. O., Marquart, H., Hansen, T. M., Sorensen, S. F., Petersen, J., Volck, B., Svejgaard, A., Graudal, N. A., Rudd, P. M., Dwek, R. A., Sim, R. B. and Andersen, V., 2000. Two edged role of mannose binding lectin in rheumatoid arthritis: a cross sectional study. J. Rheumatol. 2:7, 26.
25. Gherghiceanu, M., Penescu, M. and Mandache, E., 2005. The predictive value of peritubular capillaries C3d deposition in IgA glomerulonephritis. J. Cell Mol. Med. 9, 143.,
26. Gorni, K., Tokue, Y., Kobayashi, T., Takahashi, H., Watanabe, A., Fujita, T. and Nukiwa, T., 2004. Mannose-binding lectin gene polymorphism is a modulating factor in repeated respiratory infections. Chest 126, 95.
27. Gupta, B., Agrawal, C., Raghav, S. K., Das, S. K., Das, R. H., Chaturvedi, V. P. and Das, H. R., 2005. Association of mannose-binding lectin gene (MBL2) polymorphisms with rheumatoid arthritis in an Indian cohort of case-control samples. J. Hum. Genet. 50, 583.
28. Hansen, T. K., Tarnow, L., Thiel, S., Steffensen, R., Stehouwer, C. D., Schalkwijk, C. G., Parving, H. H. and Flyvbjerg, A., 2004. Association between mannose-binding lectin and vascular complications in type 1 diabetes. Diabetes 53, 1570.

29. Hansen, T. K., Thiel, S., Knudsen, S. T., Gravholt, C. H., Christiansen, J. S., Mogensen, C. E. and Poulsen, P. L., 2003. Elevated levels of mannan-binding lectin in patients with type 1 diabetes. J. Clin. Endocrinol. Metab 88, 4857.
30. Hart, M. L., Ceonzo, K. A., Shaffer, L. A., Takahashi, K., Rother, R. P., Reenstra, W. R., Buras, J. A. and Stahl, G. L., 2005. Gastrointestinal ischemia-reperfusion injury is lectin complement pathway dependent without involving C1q. J. Immunol. 174, 6373.
31. Hegele, R. A., Ban, M. R., Anderson, C. M. and Spence, J. D., 2000. Infection-susceptibility alleles of mannose-binding lectin are associated with increased carotid plaque area J. Investig. Med. 48, 198.
32. Hisano, S., Matsushita, M., Fujita, T., Endo, Y. and Takebayashi, S., 2001. Mesangial IgA2 deposits and lectin pathway-mediated complement activation in IgA glomerulonephritis. Am. Kidney Dis. 38, 1082.
33. Hovind, P., Hansen, T. K., Tarnow, L., Thiel, S., Steffensen, R, Flyvbjerg, A. and Parving, H. H., 2005. Mannose-binding lectin as a predictor of microalbuminuria in type 1 diabetes: an inception cohort study. Diabetes 54, 1523.
34. Kaur, S., Gupta, V. K., Shah, A., Thiel, S., Sarma, P. U. and Madan, T., 2006. Elevated levels of mannan-binding lectin [corrected] (MBL) and eosinophilia in patients of bronchial asthma with allergic rhinitis and allergic bronchopulmonary aspergillosis associate with a novel intronic polymorphism in MBL. Clin. Exp. Immunol. 143, 414.
35. Kuipers, S., Aerts, P. C., Cluysenaer, O. J., Bartelink, A. K., Ezekowitz, R. A., Bax, W. A., Salimans, M. and Vandyk, H., 2003. A case of familial meningococcal disease due to deficiency in mannose-binding lectin (MBL). Adv. Exp. Med. Biol. 531, 351.
36. Lhotta, K., Wurzner, R., Rumpelt, H. J., Eder, P. and Mayer, G., 2004. Membranous nephropathy in a patient with hereditary complete complement C4 deficiency. Nephrol. Dial. Transplant. 19, 990.
37. Madsen, H. O., Garred, P., Thiel, S., Kurtzhals, J. A., Lamm, L. U., Ryder, L. P. and Svejgaard, A., 1995. Interplay between promoter and structural gene variants control basal serum level of mannan-binding protein. J. Immunol. 155, 3013.
38. Madsen, H. O., Videm, V., Svejgaard, A., Svennevig, J. L. and Garred, P., 1998. Association of mannose-binding-lectin deficiency with severe atherosclerosis. Lancet 352, 959.
39. Matsushita, M., Endo, Y. and Fujita, T., 2000. Cutting edge: complement-activating complex of ficolin and mannose-binding lectin-associated serine protease. J. Immunol. 164, 2281.
40. Moller-Kristensen, M., Ip, W. K., Shi, L., Gowda, L. D., Hamblin, M. R., Thiel, S., Jensenius, J. C., Ezekowitz, R. A. and Takahashi, K., 2006. Deficiency of mannose-binding lectin greatly increases susceptibility to postburn infection with *Pseudomonas aeruginosa*. J. Immunol. 176, 1769.
41. Moller-Kristensen, M., Jensenius, J. C., Jensen, L., Thielens, N., Rossi, V., Arlaud, G; and Thiel, S., 2003. Levels of mannan-binding lectin-associated serine protease-2 in healthy individuals. J. Immunol. Methods 282, 159.
42. Neth, O., Hann, I., Turner, M. W. and Klein, N. J., 2001. Deficiency of mannose-binding lectin and burden of infection in children with malignancy: a prospective study. Lancet 358, 614.
43. Ohlenschlaeger, T., Garred, P., Madsen, H. O. and Jacobsen, S., 2004. Mannose-binding lectin variant alleles and the risk of arterial thrombosis in systemic lupus erythematosus. N. Engl. J. Med. 351, 260.
44. Petersen, S. V., Thiel, S., Jensen, L., Steffensen, R. and Jensenius, J. C., 2001. An assay for the mannan-binding lectin pathway of complement activation. J. Immunol. Methods 257, 107.
45. Petersen, S. V., Thiel, S., Jensen, L., Vorup-Jensen, T., Koch, C. and Jensenius, J. C., 2000. Control of the classical and the MBL pathway of complement activation. Mol. Immunol. 37, 803.
46. Reis, S., Falcao, D. A. and Isaac, L., 2006a. Clinical aspects and molecular basis of primary deficiencies of complement component C3 and its regulatory proteins factor I and factor H. Scand. J. Immunol. 63, 155.
47. Reis, S., Falcao, D. A. and Isaac, L., 2006b. Clinical aspects and molecular basis of primary deficiencies of complement component C3 and its regulatory proteins factor I and factor H. Scand. J. Immunol. 63, 155.
48. Roos, A., Bouwman, L. H., Munoz, J., Zuivenloof, T., Faber-Krol, M. C., Fallaux-van den Houten F C, Klar-Mohamad, N., Hack, C. E., Tilanus, M. G. and Daha, M. R, 2003. Functional characterization of the lectin pathway of complement in human serum. Mol. Immunol. 39, 655.
49. Roos, A., Bouwman, L. H., van Gijlswijk-Janssen, D. J., Faber-Krol, M. C., Stahl, G. L. and Daha, M. R., 2001. Human IgA activates the complement system via the mannan-binding lectin pathway. J. Immunol. 167, 2861.
50. Roos, A., Rastaldi, M. P., Calvaresi, N., Oortwijn, B. D., Schlagwein, N., van Gijlswijk-Janssen, D. J., Stahl, G. L., Matsushita, M., Fujita, T., van, K. C. and Daha, M. R., 2006. Glomerular activation of the lectin pathway of complement in IgA nephropathy is associated with more severe renal disease. J. Am. Soc. Nephrol. 17, 1724.
51. Rossi, V., Cseh, S., Bally, I., Thielens, N. M., Jensenius, J. C. and Arlaud, G. J., 2001. Substrate specificities of recombinant mannan-binding lectin-associated serine proteases-1 and -2. J. Biol. Chem. 276, 40880.
52. Rossi, V., Teillet, F., Thielens, N. M., Bally, I. and Arlaud, G. J., 2005. Functional characterization of complement proteases C1s/mannan-binding lectin-associated serine protease-2 (MASP-2) chimeras reveals the higher C4 recognition efficacy of the MASP-2 complement control protein modules. J. Biol. Chem. 280, 41811.
53. Saevarsdottir, S., Oskarsson, O. O., Aspelund, T., Eiriksdottir, G., Vikingsdottir, T., Gudnason, V. and Valdimarsson, H., 2005. Mannan binding lectin as an adjunct to risk assessment for myocardial infarction in individuals with enhanced risk. J. Exp. Med. 201, 117.
54. Saevarsdottir, S., Vikingsdottir, T., Vikingsson, A., Manfredsdottir, V., Geirsson, A. J. and Valdimarsson, H., 2001. Low mannose binding lectin predicts poor prognosis in patients with early rheumatoid arthritis. A prospective study. J. Rheumatol. 28, 728.
55. Scudiero, O., Nardone, G., Omodei, D., Tatangelo, F., Vitale, D. F., Salvatore, F. and Castaldo, G., 2006. A mannose-binding lectin-defective haplotype is a risk factor for gastric cancer. Clin. Chem. 52, 1625.
56. Seelen, M. A., Roos, A., Wieslander, J., Mollnes, T. E., Sjoholm, A. G., Wurzner, R., Loos, M., Tedesco, F., Sim, R. B., Garred, P., Alexopoulos, E., Turner, M. W. and Daha, M. R., 2005a. Functional analysis of the classical, alternative, and MBL pathways of the complement system: standardization and validation of a simple ELISA. J. Immunol. Methods 296, 187.
57. Seelen, M. A., van der Bijl, E. A., Trouw, L. A., Zuiverloon, T. C., Munoz, J. R., Fallaux-van den Houten E C., Schlagwein, N., Daha, M. R., Huizinga, T. W. and Roos, A., 2005b. A role for mannose-binding lectin dysfunction in generation of autoantibodies in systemic lupus erythematosus. Rheumatology. (Oxford) 44, 11.1.
58. Selander, B., Martensson, U., Weintraub, A., Holmstrom, E., Matsushita, M., Thiel, S., Jensenius, J. C., Truedsson, L. and Sjoholm, A. G., 2006. Mannan-binding lectin activates C3 and the alternative complement pathway without involvement of C2. J. Clin. Invest 116, 1425.
59. Sjoholm, A. G., Jonsson, G., Braconier, J. H., Sturfelt, G. and Truedsson, L., 2006. Complement deficiency and disease: an update. Mol. Immunol. 43, 78.
60. Souza; D. G., Esser, D., Bradford, R., Vieira, A. T. and Teixeira, M. M., 2005. APT070 (Mirococept), a membrane-localised complement inhibitor, inhibits inflammatory responses that follow intestinal ischaemia and reperfusion injury. Br. J. Pharmacol. 145, 1027.
61. Spence, J. D. and Norris, J., 2003. Infection, inflammation, and atherosclerosis. Stroke 34, 333.
62. Stahl, G. L., Xu, Y., Hao, L., Miller, M., Buras, J. A., Fung, M. and Zhao, H., 2003. Role for the alternative complement pathway in ischemia/reperfusion injury. Am. J. Pathol. 162, 449.
63. Steffensen, R., Thiel, S., Varming, K., Jersild, C. and Jensenius, J. C., 2000. Detection of structural gene mutations and promoter polymorphisms in the mannan-binding lectin (MBL) gene by polymerase chain reaction with sequence-specific primers. J. Immunol. Methods 241, 33.
64. Suzuki, J., Suzuki, S., Nozawa, R., Kawasaki, Y. and Suzuki, H., 2003. Membranoproliferative glomerulonephritis associated with hereditary deficiency of the 4th component of complement. Clin. Nephrol. 60, 279.
65. Szeplaki, G., Varga, L., Laki, J., Dosa, E., Madsen, H. O., Prohaszka, Z., Szabo, A., Acsady, G., Selmeci, L., Garred, P., Fust, G. and Entz, L., 2006. Elevated complement C3 is associated with early restenosis after eversion carotid endarterectomy. Thromb. Haemost. 96, 529.
66. Takahashi, R., Tsutsumi, A., Ohtani, K., Muraki, Y., Goto, D., Matsumoto, I., Wakamiya, N. and Sumida, T., 2005. Association of mannose binding lectin (MBL) gene polymorphism and serum MBL concentration with characteristics and progression of systemic lupus erythematosus. Ann. Rheum. Dis. 64, 311.
67. Teillet, F., Dublet, B., Andrieu, J. P., Gaboriaud, C., Arlaud, G. J. and Thielens, N. M., 2005. The two major oligomeric forms of human mannan-binding lectin: chemical characterization, carbohydrate-binding properties, and interaction with MBL-associated serine proteases. J. Immunol. 174, 2870.
68. Terai, I., Kobayashi, K., Matsushita, M., Miyakawa, H., Mafune, N. and Kikuta, H., 2003. Relationship between gene polymorphisms of mannose-binding lectin (MBL) and two molecular forms of MBL. Eur. J. Immunol. 33, 2755.
69. Thiel, S., Moller-Kristensen, M., Jensen, L. and Jensenius, J. C., 2002. Assays for the functional activity of the mannan-binding lectin pathway of complement activation. Immunobiology 205, 446.
70. Tosic, L., Sutherland, W. M., Kurek, J., Edberg, J. C. and Taylor, R. P., 1989. Preparation of monoclonal antibodies to C3b by immunization with C3b(i)-sepharose. J. Immunol. Methods 120, 241.
71. van Emmerik, L. C., Kuijper, E. J., Fijen, C. A., Dankert, J. and Thiel, S., 1994. Binding of mannan-binding protein to various bacterial pathogens of meningitis. Clin. Exp. Immunol. 97, 411.
72. Verma, A., Matta, A., Shukla, N. K., Deo, S. V., Gupta, S. D. and Ralhan, R., 2006. Clinical significance of mannose-binding lectin-associated serine protease-2 expression in esophageal squamous cell carcinoma. Int. J. Cancer 118, 2930.
73. Walport, M. J., 2001a. Complement. First of to parts. N. Eng. J. Med. 344, 1058.
74. Walport, M. J., 2001b. Complement. Second of two parts. N. Engl. J. Med. 344, 1140.
75. Weisman, H. F., Bartow, T., Leppo, M. K., Boyle, M. P., Marsh, H. C., Jr., Carson, G. R., Roux, K. H., Weisfeldt, M. L. and Fearon, D. T., 1990. Recombinant soluble CR1 suppressed complement activation, inflammation, and necrosis associated with reperfusion of ischemic myocardium. Trans. Assoc. Am. Physicians 103, 64.
76. Yang, Y., Lhotta, K., Chung, E. K., Eder, P., Neumair, F. and Yu, C. Y., 2004. Complete complement components C4A and C4B deficiencies in human kidney diseases and systemic lupus erythematosus. J. Immunol. 173, 2803.
77. Ytting, H., Christensen, I. J., Jensenius, J. C.; Thiel, S., and Nielsen, H. J., 2005. Preoperative mannan-binding lectin pathway and prognosis in colorectal cancer. Cancer Immunol. Immunother. 54, 265.
78. Zhang, H., Zhou, G., Zhi, L., Yang, H., Zhai, Y., Dong, X., Zhang, X., Gao, X., Zhu, Y. and He, F., 2005; Association between mannose-binding lectin gene polymorphisms and susceptibility to severe acute respiratory syndrome coronavirus infection. J. Infect. Dis. 192, 1355.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The listing of references herein is not intended to be an admission that any of the references is a prior art reference.

What is claimed is:

1. A method of assessing lectin complement pathway (LCP) activation, comprising:
   determining an amount of mannose binding lectin (MBL) in a biological sample,
   removing non-covalently bound MBL/mannose binding lectin serine protease 2 (MASP-2) complexes,
   determining an amount of another LCP component in the biological sample, and
   assessing LCP activation in the biological sample based on the amounts of MBL and the another component.

2. The method of claim 1, wherein the another LCP component is, C3, C3b, C4, C4b or C4b/2a.

3. The method of claim 2, wherein the method further comprises:
   measuring a further LCP component in the biological sample.

4. The method of claim 3, wherein the further LCP component is MASP-2, C3, C3b, C4, C4b or C4b/2a.

5. The method of claim 4, wherein the another LCP component is C4 and the further LCP component is C3.

6. The method of claim 4, wherein still another LCP component is measured in the biological sample.

7. The method of claim 6, wherein the still other LCP component is MASP-2.

8. The method of claim 1, wherein the non-covalently bound MBL/MASP-2complexes are removed with the addition of a buffer that contains a calcium chelator.

9. The method of claim 8, wherein the calcium chelator is EDTA or EGTA.

10. The method of claim 8, wherein the buffer further contains a competitive inhibitor of MBL.

11. The method of claim 10, wherein the competitive inhibitor is mannose, N-acetylglucosamine (GlcNAc), fucose, glucose or an anti-MBL antibody.

12. The method of claim 1, wherein the biological sample is a serum, plasma or cerebrospinal fluid sample.

13. The method of claim 1, wherein the biological sample is from a subject with or suspected of having LCP-mediated disease.

14. The method of claim 1, wherein the measurements are performed in the same biological sample or portion thereof.

15. A method of assessing LCP activation, comprising:
contacting a substrate coated with a ligand of MBL with a biological sample,
contacting the sample with a detectably labeled agent that specifically binds MBL,
determining the amount of MBL present,
removing non-covalently bound MBL/MASP-2 complexes from the sample,
contacting the sample with a detectably labeled agent that specifically binds C4,
contacting the sample with a detectably labeled agent that specifically binds C3,
determining the amount of C4 and C3 present, and
assessing LCP activation in the sample based on the amounts of MBL, C4 and C3.

16. The method of claim 15, wherein the ligand of MBL is mannan, mannose or GlcNAc.

17. The method of claim 15, wherein the agent that specifically binds MBL is an anti-MBL antibody.

18. The method of claim 15, wherein the agent that specifically binds C4 is an anti-C4 antibody.

19. The method of claim 15, wherein the agent that specifically binds C3 is an anti-C3 antibody.

20. The method of claim 15, wherein the method further comprises:
contacting the sample with a detectably labeled agent that specifically binds MASP-2, and determining the amount of MASP-2 present.

21. The method of claim 20, wherein the agent that specifically binds MASP-2 is an anti-MASP-2 antibody.

22. The method of claim 15, wherein the biological sample is a serum, plasma or cerebrospinal fluid sample.

23. The method of claim 15, wherein the biological sample is from a subject with or suspected of having a LCP-mediated disease.

24. The method of claim 15, wherein the measurements are performed in the same well of a well plate.

* * * * *

UNITED STATES PATENT AND TRADEMARK OFFICE
CERTIFICATE OF CORRECTION

Page 1 of 1

PATENT NO. : 8,524,453 B2
APPLICATION NO. : 12/223763
DATED : September 3, 2013
INVENTOR(S) : Gregory L. Stahl et al.

It is certified that error appears in the above-identified patent and that said Letters Patent is hereby corrected as shown below:

In the Claims

At column 34, claim 2, lines 54-55, please delete "component is, C3" and replace with --component is C3--.

At column 34, claim 7, line 66, please delete "still other" and replace with --still another--.

At column 35, claim 8, line 2, please delete "MBL/MASP-2complexes" and replace with --MBL/MASP-2 complexes--.

Signed and Sealed this
First Day of September, 2015

Michelle K. Lee
*Director of the United States Patent and Trademark Office*